US012623042B2

(12) United States Patent
Salvino et al.

(10) Patent No.: US 12,623,042 B2
(45) Date of Patent: *May 12, 2026

(54) ENDOTRACHEAL TUBE RELIEF VALVE

(71) Applicants: Chris Salvino, Scottsdale, AZ (US);
Keir Hart, Lafayette, CO (US);
Frederick Austin, Boulder, CO (US)

(72) Inventors: Chris Salvino, Scottsdale, AZ (US);
Keir Hart, Lafayette, CO (US);
Frederick Austin, Boulder, CO (US)

(73) Assignee: SharpMed, LLC., Scottsdale, AZ (US)

( * ) Notice: Subject to any disclaimer, the term of this
patent is extended or adjusted under 35
U.S.C. 154(b) by 0 days.

This patent is subject to a terminal disclaimer.

(21) Appl. No.: 17/947,453

(22) Filed: Sep. 19, 2022

(65) Prior Publication Data

US 2023/0014924 A1    Jan. 19, 2023

Related U.S. Application Data

(63) Continuation-in-part of application No. 17/724,465,
filed on Apr. 19, 2022, now Pat. No. 11,826,507,
(Continued)

(51) Int. Cl.
*A61M 16/08* (2006.01)
*A61M 16/00* (2006.01)
*A61M 16/20* (2006.01)

(52) U.S. Cl.
CPC .... *A61M 16/0816* (2013.01); *A61M 16/0051*
(2013.01); *A61M 16/209* (2014.02)

(58) Field of Classification Search
CPC .............. A61M 16/04; A61M 16/0463; A61M
16/0475; A61M 16/0816; A61M 16/0833;
(Continued)

(56) References Cited

U.S. PATENT DOCUMENTS 3,667,475 A * 6/1972 Venturelli ......... A61M 16/0463
128/207.14
4,327,721 A * 5/1982 Goldin .............. A61M 16/0486
128/207.15
(Continued)

FOREIGN PATENT DOCUMENTS

CN 110496285 A * 11/2019
DE 102007062861 A1 * 6/2009 .......... A61M 16/044
(Continued)

*Primary Examiner* — Kathryn E Ditmer
(74) *Attorney, Agent, or Firm* — Kenneth Altshuler

(57) ABSTRACT

A non-ventilator ET tube cap used to oxygenate a patient
during an intubation procedure. The ET tube cap generally
comprises an oxygen source connector configured to connect to an oxygen source via an oxygen tube. This provides
oxygen to a patient via an ET tube while being intubated.
The ET tube cap further includes an ET tube receiving
aperture that is specifically arranged to engage an ET tube in
a removable relationship prior to the ET tube connected to
a ventilator while the ET tube is deployed in a patient.
Optionally, the ET tube cap can comprise at least two
pressure relief valves that open when pressure inside of the
ET tube cap exceeds a predetermined pressure threshold to
prevent harm to the patient that is being intubated.

9 Claims, 29 Drawing Sheets

1240

Related U.S. Application Data which is a continuation-in-part of application No. 16/986,666, filed on Aug. 6, 2020, now abandoned.

(60) Provisional application No. 62/883,335, filed on Aug. 6, 2019.

(58) Field of Classification Search
CPC .. A61M 16/209; A61M 39/20; A61M 39/205; A61M 2202/0208
See application file for complete search history.

(56) References Cited

U.S. PATENT DOCUMENTS

| | | | |
|---|---|---|---|
| 4,350,647 A * | 9/1982 | de la Cruz | A61M 16/209 |
| | | | 137/859 |
| 5,183,031 A * | 2/1993 | Rossoff | A61B 1/267 |
| | | | 600/164 |
| 5,329,940 A * | 7/1994 | Adair | A61B 1/2676 |
| | | | 128/207.14 |
| 5,458,139 A * | 10/1995 | Pearl | A61M 16/0463 |
| | | | 128/207.14 |
| 5,509,408 A * | 4/1996 | Kurtis | A61M 16/0484 |
| | | | 128/207.14 |
| 5,701,918 A * | 12/1997 | Jiraki | A61B 42/00 |
| | | | 606/1 |
| 6,196,225 B1 | 3/2001 | Allgeyer | |
| 6,319,195 B1 * | 11/2001 | Nakaichi | A61B 1/267 |
| | | | 600/150 |
| 6,568,388 B2 | 5/2003 | Christopher | |
| 6,631,713 B1 | 10/2003 | Christopher | |
| 6,895,966 B2 | 5/2005 | Christopher | |
| 7,921,847 B2 | 4/2011 | Totz | |
| 8,747,306 B1 * | 6/2014 | Ramos | A61B 42/20 |
| | | | 600/197 |
| 9,220,859 B2 | 12/2015 | Li et al. | |
| 9,968,750 B2 | 5/2018 | Sinderby et al. | |
| 10,434,272 B1 * | 10/2019 | Annis | A61B 1/267 |
| 2003/0047189 A1 | 3/2003 | Kumar et al. | |
| 2003/0188749 A1 | 10/2003 | Nichols et al. | |
| 2005/0139220 A1 | 6/2005 | Christopher | |
| 2005/0263157 A1 * | 12/2005 | Olsen | A61M 16/049 |
| | | | 128/206.28 |
| 2005/0279360 A1 * | 12/2005 | Wei | A61M 16/0486 |
| | | | 128/207.14 |
| 2011/0139151 A1 * | 6/2011 | Burns | A61M 16/0875 |
| | | | 128/207.14 |
| 2012/0191037 A1 * | 7/2012 | Patel | F16K 5/0407 |
| | | | 604/246 |
| 2013/0081616 A1 * | 4/2013 | Tatkov | A61M 16/0057 |
| | | | 128/201.13 |
| 2013/0085325 A1 * | 4/2013 | Fuller | A61M 1/76 |
| | | | 600/102 |
| 2015/0306329 A1 * | 10/2015 | Brown | A61M 16/0463 |
| | | | 128/200.26 |
| 2016/0256646 A1 * | 9/2016 | Vazales | A61M 13/003 |
| 2018/0280641 A1 | 10/2018 | White et al. | |
| 2018/0361092 A1 * | 12/2018 | Crowell | A62B 7/00 |

FOREIGN PATENT DOCUMENTS

| | | | | |
|---|---|---|---|---|
| WO | WO-9303777 A1 * | 3/1993 | | A61M 16/0488 |
| WO | WO-9530448 A1 * | 11/1995 | | A61M 16/04 |
| WO | WO-9829153 A1 * | 7/1998 | | A61M 16/06 |
| WO | WO-2018195656 A1 * | 11/2018 | | A61M 16/0434 |

\* cited by examiner

<u>100</u>

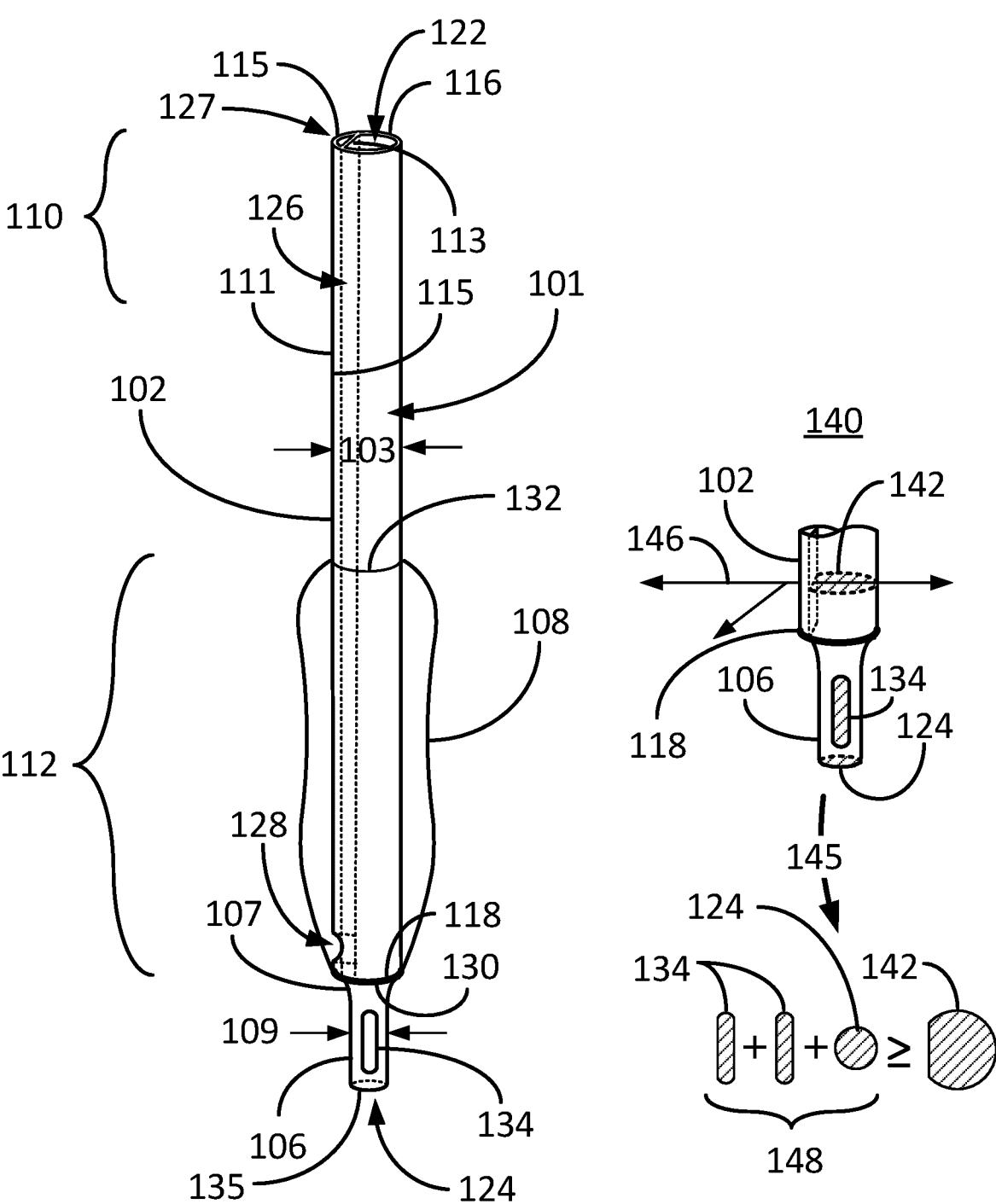
FIG. 2A     FIG. 2B

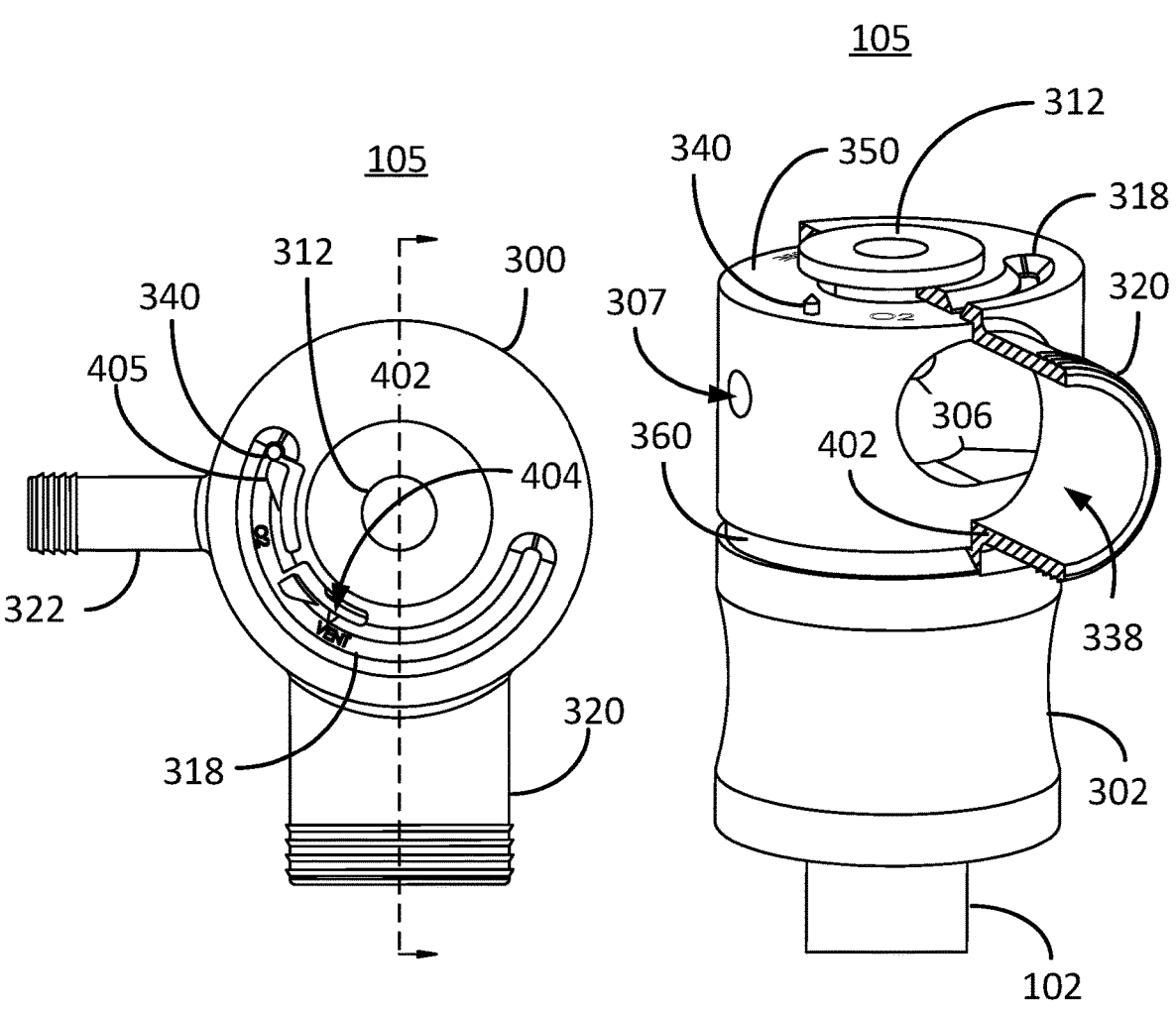
FIG. 4A          FIG. 4B

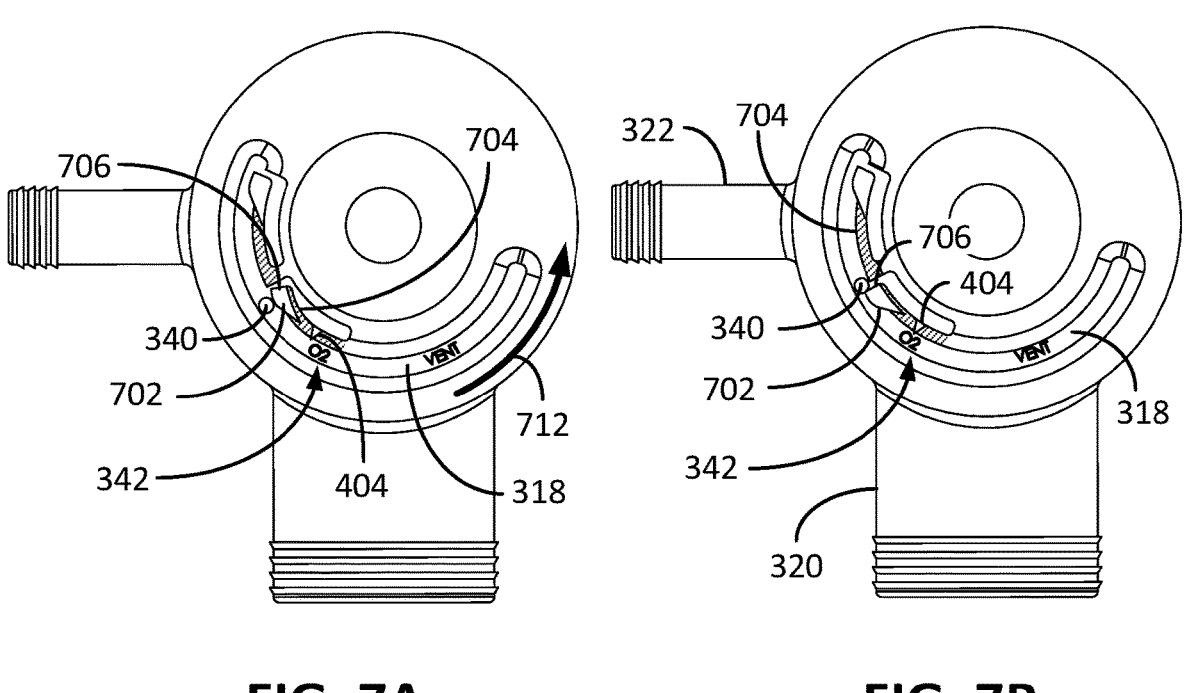
FIG. 7A     FIG. 7B

1100

1200

1200

1200

1101

1130    1102    1103

1108    1106

1214

1215b    1215a 1122    1110

1112

SECTION C-C

1104

SECTION D-D

1140

1240

ENDOTRACHEAL TUBE RELIEF VALVE

CROSS-REFERENCE TO RELATED APPLICATIONS

This continuation-in-part application which claims priority to and the benefit of U.S. patent application Ser. No. 17/724,465 entitled: Endotracheal Tube Assembly, filed on Apr. 19, 2022, which claims priority to and the benefit of U.S. patent application Ser. No. 16/986,666 entitled: Endotracheal Tube Assembly, filed on Aug. 6, 2020, which claims priority to and the benefit of U.S. Provisional Patent Application No. 62/883,335 entitled: Endotracheal Tube Assembly, filed on Aug. 6, 2019.

FIELD OF THE INVENTION

The present embodiments are directed to a multipurpose endotracheal tube that improves deployment in a patient and long-term comfort to the patient.

DESCRIPTION OF RELATED ART

Whether for trauma, serious illness or surgery with a general anesthetic, endotracheal tubes are a common device for providing oxygen to people in distress. An endotracheal tube is a flexible plastic tube that threads into a person's windpipe (trachea) to assist the person in breathing. Typically, once deployed in a person, endotracheal tubes connect to a ventilator to deliver oxygen to their lungs. Endotracheal tubes come in a number of different sizes ranging from 2.0 mm to 10.5 mm in diameter. Typically, most women use a 6.0-7.5 mm diameter tube and most men use a 7.0-9 mm tube. The outer diameter dictates the tube size and an inflatable balloon/cuff near the end of the endotracheal tube varies in volume and diameter, depending on the patient's anatomy. Presently, a single sized inflatable cuff is deployed between a patient's lungs and vocal cords (and more specifically below the vocal cords). An endotracheal tube is sized for a patient based on the space between the vocal cords, which in men is typically larger than in women. Choosing an endotracheal tube size (diameter) is based on experience and guess work. The inflatable cuff retains the endotracheal tube (ET tube) in a patient, once deployed, and helps prevent regurgitation from entering the patient's lungs. In emergency situations while in an operating room doctors have to guess of the right size ET tube, which is generally chosen based on age and body weight.

During an intubation procedure (where a patient is actively having an endotracheal inserted down their trachea), medical personnel sometimes have trouble positioning the end of the endotracheal tube in the right position through a patient's vocal cords. Accordingly, excess time in deploying an ET tube jeopardizes the safety of an already oxygen deprived (not breathing) patient. Nonetheless, once the patient is intubated (the activity of having an ET tube deployed), the ET tube is connected to a ventilator which feeds oxygen to the patient.

Though patients can be intubated for short periods of time, such as during surgery when they are under anesthesia and temporarily paralyzed, some very ill patients are intubated for prolonged periods of time, such as weeks. Prolonged intubation can harm people's vocal cords in addition to causing other problems.

It is to innovations related to this subject matter that the embodiments invention is generally directed.

SUMMARY OF THE INVENTION

The present embodiments are directed to multipurpose endotracheal tubes, that among other benefits improve deployment in a patient, improves oxygenation to the patient upon deployment and further improves long-term comfort.

Certain embodiments of the present invention contemplate an endotracheal tube comprising: a main flexible hollow endotracheal tube that extends in a constant tube diameter from a proximal endotracheal tube end, defined by an inlet port, to a transition zone; a tip that extends from the transition zone to a distal endotracheal tube end defined by an outlet port; an uninterrupted pathway extending between the inlet port and the outlet port; and at least one tip side aperture in the tip between the transition zone and the outlet port, the at least one tip side aperture in communication with the uninterrupted pathway, the tip possessing a tip diameter that is at least 20% smaller than the constant tube diameter.

Yet other certain embodiments of the present invention contemplate an endotracheal tube comprising: a tip that extends from a flexible hollow endotracheal tube, the flexible hollow endotracheal tube having a constant tube outer diameter, the tip tapering from the constant tube outer diameter to a tip outer diameter that is less than 10% smaller than the constant tube outer diameter; an uninterrupted pathway extending between an inlet port located at a proximal end of the a flexible hollow endotracheal tube and an outlet port located at a distal end of the tip; and at least two tip side apertures defined by apertures in a side of the tip between the constant outer tube diameter and the outlet port, the tip side apertures in communication with the uninterrupted pathway.

While other certain embodiments of the present invention contemplate an endotracheal tube apparatus comprising: a flexible hollow endotracheal tube that extends between a first tube end and a second tube end, the endotracheal tube is essentially defined by a constant tube diameter, the first end possessing a tube inlet port; and a tip joined with the endotracheal tube at the second tube end, the tip tapered from a first tip diameter where the tip is joined with the second end to a second tip diameter at essentially a tip distal end, the second tip diameter smaller than the first tip diameter, the tip distal end terminating in a tip distal outlet port, the tip including at least one tip side port located between where the tip is joined with the second end and the distal end, the tube inlet port is in communication with the tip distal outlet port and the at least one tip side port via a contiguous passageway.

Other embodiments of the present invention contemplate an endotracheal tube cap arrangement comprising: a cylindrically shaped inlet body having a hollow core; a cuff inflation aperture passing through a side wall of the inlet body into a cuff inflation pathway; a ventilation aperture passing through the side wall to the hollow core; a cap rotatingly engaged with the inlet body (engaged in a rotating relationship), the cap covering an upper portion of the inlet body that includes the cuff inflation aperture and the ventilation aperture; an oxygen inlet tube defining an oxygen inlet passageway extending from the cap and a ventilation tube defining a ventilation tube passageway extending from the cap, when the cap is in a first rotational position on the inlet body the oxygen inlet passageway is aligned with the cuff inflation aperture, when the cap is in a second rotational position on the inlet body the ventilation tube passageway is aligned with the ventilation aperture, the cap arrangement configured to matingly connect (connect in a mating relationship) with a proximal end of an endotracheal tube.

Yet other certain embodiments of the present invention contemplate a method comprising: providing an endotracheal tube cap arrangement that has a cylindrically shaped inlet body with a hollow core, a cuff inflation aperture passing through a side wall of the inlet body into a cuff inflation pathway, a ventilation aperture passing through the side wall to the hollow core, a cap rotatingly engaged (in a rotating manner) with the inlet body, the cap covering an upper portion of the inlet body that includes the cuff inflation aperture and the ventilation aperture, an oxygen inlet tube extending from the cap and defining an oxygen inlet passageway and a ventilation tube also extending from the cap and defining a ventilation tube passageway, and an endotracheal tube matingly connected (engaged in a mating relationship) to a bottom side of the inlet body; connecting a first air hose to the oxygen inlet tube and a second air hose to the ventilation tube; rotating the cap in a first position where the oxygen inlet tube is in line with the ventilation aperture, but not in line with the cuff inflation aperture and the ventilation tube is not in line with any of the apertures; and deploying the endotracheal tube into a trachea while air supplied by the first air hose is moving through the oxygen inlet passageway, through the ventilation aperture, through the hollow core and through an exit port of the endotracheal tube.

While still other certain embodiments of the present invention contemplate a method comprising: providing an endotracheal tube cap arrangement that includes a rotatable cap that possesses an enriched oxygen source and a ventilation air source, and an endotracheal tube connected to the endotracheal tube cap arrangement; with the endotracheal tube cap arrangement in a first position moving enriched oxygen from the enriched oxygen source through an exit port of the endotracheal tube; intubating a trachea while the enriched oxygen is moving through the exit port, and while ventilation air is blocked from the ventilation air source.

Some other embodiments of the present invention contemplate a non-ventilator ET tube cap comprising: an oxygen source connector that connects to an oxygen source via an oxygen tube, the oxygen source configured to flow oxygen into through an ET tube; an ET tube receiving aperture that is that engages the ET tube in a removable relationship; and at least two pressure relief valves that open when pressure from the oxygen in the ET tube exceeds a predetermined pressure threshold.

BRIEF DESCRIPTION OF THE DRAWINGS

FIG. 2A illustratively depicts the endotracheal tube apparatus without the cap body assembly consistent with embodiments of the present invention;

FIG. 2B illustratively depicts the outlet port area related to the main endotracheal tube area consistent with embodiments of the present invention;

FIGS. 4A and 4B are line drawings of a cross-section of a cap body assembly consistent with embodiments of the present invention;

FIGS. 7A-7C illustratively depict line drawings of the endotracheal tube apparatus embodiment with the cap rotated in the O2 cuff setting consistent with embodiments of the present invention;

DETAILED DESCRIPTION

Figure 1:
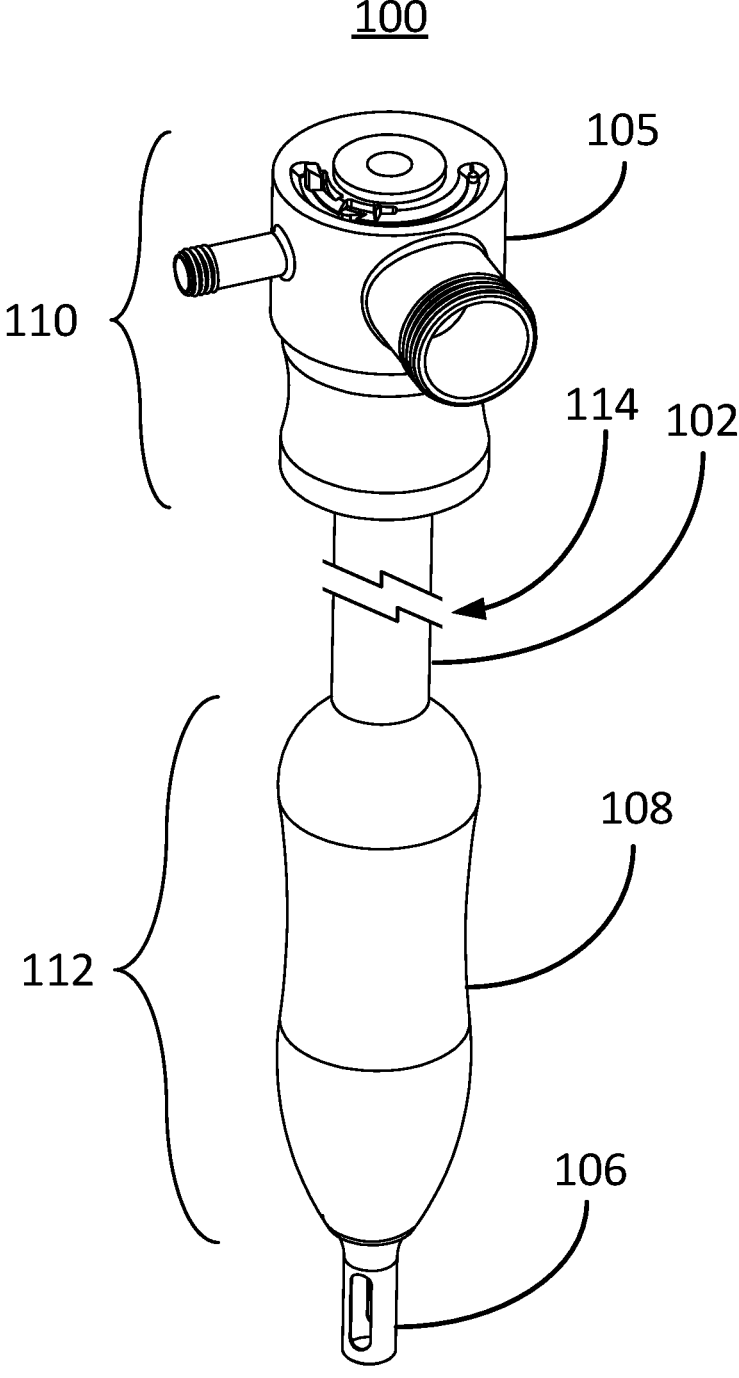
FIG. 1 illustratively depicts a line drawing of an endotracheal tube apparatus consistent with embodiments of the present invention.

Initially, this disclosure is by way of example only, not by limitation. Thus, although the instrumentalities described herein are for the convenience of explanation, shown and described with respect to exemplary embodiments, it will be appreciated that the principles herein may be applied equally in other similar configurations involving similar uses of endotracheal tubes and endotracheal tube caps. The phrases "in one embodiment", "according to one embodiment", and the like generally mean the particular feature, structure, or characteristic following the phrase is included in at least one embodiment of the present invention, and may be included in more than one embodiment of the present invention. Importantly, such phases do not necessarily refer to the same embodiment. If the specification states a component or feature "may", "can", "could", or "might" be included or have a characteristic, that particular component or feature is not required to be included or have the characteristic. As used herein, the terms "having", "have", "including" and "include" are considered open language and are synonymous with the term "comprising". Furthermore, as used herein, the term "essentially" is meant to stress that a characteristic of something is to be interpreted within acceptable tolerance margins known to those skilled in the art when in view typical normal world tolerance, which is analogous with "more or less." For example, essentially flat, essentially straight, essentially on time, etc. all indicate that these characteristics are not capable of being perfect within the sense of their limits. Accordingly, if there is no specific +/− value assigned to "essentially", then assume essentially means to be within +/−2.5% of exact. In what follows, similar or identical structures may be identified using identical callouts.

Certain embodiments of the present invention generally relate to an endotracheal (ET) tube apparatus with improved deployment and long-term comfort for a patient, in part due to the cuff configuration. Certain ET tube embodiments generally include a cap mechanism that can direct enriched oxygen towards the patient's lungs while the ET tube apparatus is being inserted in a patient's trachea. Once the ET tube is fully inserted in the trachea, the cap mechanism can be made to redirect the enriched oxygen to inflate an inflatable cuff integrated with the ET tube, thereby blocking off the patient's vocal cord region and stabilizing the ET tube in the trachea. When the cuff is inflated, the cap mechanism can be made to ventilate the patient. Certain embodiments envision the inflatable cuff deployable above, through and below the vocal cords (unlike existing cuff that are just below the vocal cords). Some advantages allow for a universal ET tube size with further protection to vocal cords due to cushioning from the cuff. Cuff placement embodiments further reduce potential regurgitation and aspiration. With more specificity, certain embodiments of the present invention generally relate to a tracheal tube that provides improved deployment and lasting comfort. Intubation using a standard intubation tube is performed by guiding an ET tube with a laryngoscope blade into the trachea just short of the carina where the trachea branches into the lungs. Certain embodiments of the present invention contemplate providing an enriched oxygen supply positively flowing through an ET tube during an intubation procedure to provide the patient (who is being intubated) oxygen during the procedure. Oxygen during intubation provides certain improvements over the standard present day intubation procedure in that a patient can immediately start receiving oxygen. This is in contrast to present day intubation whereby a patient endures a longer period of oxygen deprivation until the ET tube is fully deployed and hooked up to an oxygen source. Accordingly, certain embodiments envision the enriched oxygen flowing through the endotracheal tube at a pressure/flow rate that will not harm the person while being intubated.

Certain other embodiments generally relate to a tip at the distal end of an ET tube that is narrowed (smaller in diameter) compared with the rest of the endotracheal tube. Some embodiments further envision side apertures, or openings, in the side of the narrowed tip in addition to the distal tip outlet port. In this way, the side apertures plus the distal tip outlet port is equal to or greater than the standard ET tube inlet/outlet tube port cross-sectional area. Furthermore, a smaller distal tip provides an added benefit of a more easily deployed ET tube, which includes ease of moving the tip of the ET tube past a patient's vocal cords. The term air used herein is defined as ambient air that includes the normal percentages of oxygen and nitrogen used to breathe, typically around 78% nitrogen and 21% oxygen +/− depending on the region and altitude. Oxygen enriched air is defined as ambient air with an increased oxygen level. For example instead of 21% oxygen, oxygen enriched air may be 40%, 60%, 90% or close to 100% oxygen by volume (with any balance being a lower percentage of nitrogen or other gas).

Additional embodiments generally relate to a rotatable cap, or other similar air adjustment means integrated with an ET tube, that serves as a single mechanism for providing pressurized air for various ET tube components during different steps of the intubation process. In certain embodiments, a rotatable cap can be connected to 1) a ventilation tube that is connected to a ventilator (which provides a ventilation air source), and 2) an oxygen tube that is connected to an enriched oxygen source (such as oxygen concentrations greater than ambient air). The rotatable cap can be initially set so that enriched oxygen from the enriched oxygen source positively flows through an ET tube while a patient is intubated thereby providing the patient desperately needed oxygen the moment the intubation tube is inserted in their trachea. Next, when the ET tube is essentially completely inserted in position (approximately 2 cm above the carina in a trachea), the cap is rotated in a second position to inflate a cuff attached to the endotracheal tube to hold the ET tube in place. The cuff expanding at the vocal cords. Finally, the cap is rotated in a third position to start the ventilation process.

Still other embodiments envision a non-ventilator ET tube cap used to oxygenate a patient during an intubation procedure. The ET tube cap generally comprises an oxygen source connector configured to connect to an oxygen source via an oxygen tube. This provides oxygen to a patient via an ET tube while being intubated. The ET tube cap further includes an ET tube receiving aperture that is specifically arranged to engage an ET tube in a removable relationship prior to the ET tube connected to a ventilator while the ET tube is deployed in a patient. Optionally, the ET tube cap can comprise at least one pressure relief valve that opens when pressure inside of the ET tube cap exceeds a predetermined pressure threshold to prevent harm to the patient that is being intubated.

FIG. 1 is an isometric/cut-line a line drawing of an ET tube embodiment consistent with embodiments of the present invention. Fundamentally, the ET tube apparatus 100 comprises, among other things, a main flexible hollow ET tube 102 (or just "ET tube") fixedly attached to a cap body assembly 105 at an inlet region 110, an inflatable cuff 108 at a distal region 112 and a tracheal tube tip 106. In FIG. 1, the broken lines 114 indicate that the ET tube 102 is actually much longer than depicted. The ET tube 102 must be long enough to be threaded through a patient's mouth, beyond their soft palate, through their vocal cords and into their trachea just above the carina to provide airflow to and from their lungs. For purposes of improved description, throughout the rest of the disclosure, ET tube 102 is depicted in a compressed configuration that is not realistic to its true length, which typically ranges from 20 cm to 30 cm.

FIG. 2A depicts an isometric line drawing of the ET tube apparatus 100 without the cap body assembly 105 consistent with embodiments of the present invention. As shown, the ET tube 102 extends between an upper tube end 116 and a lower tube end 118. The ET tube 102 is essentially defined by a constant outer tube diameter 103 (and inner tube diameter without taking into account the plenum 126 defined by the tube wall thickness), between the upper tube end 116 and the lower tube end 118. Furthermore, the ET tube 102 is a flexible hollow tube that is able to bend around a patient's throat. In certain embodiments, the ET tube 102 is composed of polyvinylchloride (PVC) or some other similarly flexible polymeric material within the scope and spirit of the present invention. The upper tube end 116 possesses a tube inlet port 122 through which an instrument, such as an insertion guide (e.g., metal arc) or endoscope, can be threaded therein and potentially through the ventilation passageway 101. Certain embodiments contemplate a single (universal) sized ET tube for both men and women that is accomplished by way of the narrowed tip 106, discussed in more detail below.

Presently, prior art (PA) ET tubes are typically sized differently for men and women (6.0-7.5 mm diameter tube for most women and 7.0-8.5 mm tube for most men). In PA ET tubes, the rigid diameter of the ET tube dictates the tube size and the balloon near the end of the PA ET tube varies in volume and diameter depending on the patient's anatomy. Certain embodiments of the present invention envision a common sized ET tube 102 that can range from between 5-9 mm in diameter because the inflatable cuff 108 is inflatable to different sizes. Moreover, certain inflatable cuff 108 embodiments envision a balloon below, between and above a patient's vocal cords (above a patient's vocal cords defined as between a person's vocal cords and mouth). Hence, certain inflatable cuff embodiments 108 can easily conform to different sized vocal cord openings/space, which is advantageous in a single sized ET tube 102. It is envisioned that someone with a larger diameter trachea will benefit from a cuff 108 with less air in it and someone with a smaller diameter trachea will benefit from a cuff 108 with more air in it.

The endotracheal tube apparatus 100 further comprises an endoscope tip 106 (or simply "tip") joined with the ET tube 102 at the lower tube end 118. As shown, the tip 106 is tapered 107 from the joint 130 to a smaller outer (and inner) diameter 109 at the tip distal end 135, which incidentally is also defined as the distal endotracheal tube end 135. The joint 130 and the tapered zone 107 can be a transition zone that is either linear or curved to the smaller diameter 109. Certain embodiments envision the smaller outer diameter 109 at the distal end 135 being between 10% and 50% smaller than the endotracheal tube outer diameter 103. The distal end 135 defines a distal tip outlet port 124, which is part of the ventilation passageway 101. The tip 106 further includes at least one distal tip side port 134 located between the joint 130 and the distal end 135. The tube inlet port 122 is in communication with the distal tip outlet port 124 and the distal tip side port/s 134 by way of a continuous passageway. More specifically, communication is meant that at least fluid and/or air can freely flow in the ventilation passageway 101 through the tube inlet port 122 and out the distal tip outlet port 124 and the distal tip side port/s 134 and vice versa.

As previously discussed, the single sized ET tube 102, which is configured for both men and women, that is easily threaded through their vocal cords by way of the narrowed tip 106 provides a potential for more air volume, especially to women, and eliminates the need for different diameter ET tubes.

Certain embodiments envision the tip 106 being a unitary part of the ET tube 102 that is formed by heating and pulling the distal portion of the ET tube 102 to form the smaller diameter tip 106. Other embodiments envision the smaller diameter tip 106 being a separate element from the ET tube 102 bonded to the lower tube end 118 at the joint 130 with adhesive or heat, for example.

FIG. 2B illustratively depicts the total outlet port area 148 related to the main ET tube area 142 consistent with embodiments of the present invention. In this embodiment, the distal region 140, which includes a of the main ET tube distal portion 118 and the tip 106, illustratively shows the main endotracheal tube area 142 defined in the radial plane 146. The area of the distal tip outlet port 124 and the distal tip side port/s 134 are defined by the collective area 148 of the respective apertures through which air goes in and out, depicted by the pattern fill. As shown by arrow 145, the areas of the distal tip side ports 134 in combination with the distal outlet port 124 collectively defining a total port area 148, which is greater than or equal to the main endotracheal tube area 142.

FIG. 2A further illustratively depicts an inflatable cuff 108 attached to an exterior ET tube wall 111 in the distal ET tube region 112. The ET tube-to-cuff interface 132 is an attachment/bonding point forming an airtight seal between the cuff 108 and the ET tube 102. The ET tube-to-cuff interface 132 can be sealed with glue, heat, ultrasonic welding or other bonding techniques known to those skilled in the art. Likewise, the tip-to-cuff joint 130 is an attachment point for the cuff 108 to, or near, the tip 106 (or optionally the distal region of the ET tube 102), which can also be bonded to form an airtight seal. The inflatable cuff 108 is configured to inflate to seal off the trachea at the vocal cords, and in some embodiments above and/or below as well, which improves ventilator efficiency (when connected to the ET tube apparatus 100). This can further reduce or prevent patient regurgitation from entering their lungs. In certain embodiments, the inflatable cuff 108 is thin film PVC or other elastomers made in sheets, known to those skilled in the art. In the embodiment depicted, the inflatable cuff 108 is inflated via an extruded pathway 126 formed by the inner plenum wall 113 and an inner tube lengthwise portion 115 residing in the ET tube 102. The inner plenum wall 113 can be manufactured by way of extrusion techniques. The second pathway 126 is accessible via a plenum inlet port/opening 127 (showing the inner tube portion 115, that runs lengthwise, and the inner plenum wall 113) near (within an inch or so) or at the upper ET tube end 116. The second pathway 126 extends along at least part of the length of the ET tube 102 and exits through a cuff aperture/port 128 that passes through or otherwise penetrates the side of the ET tube 102 in the distal region 112. The second pathway 126 does not communicate with the ventilation pathway 101. Certain embodiments envision the cuff port 128 being near (within 2 inches) the bottom of the lower tube end 118. Other certain embodiments envision the second pathway 126 being closed off during a heating and pulling manufacturing process if the tip 106 is formed by a heating and pulling technique of the distal portion of the ET tube 102 (to form the smaller diameter tip 106).

In essence, the configuration of FIG. 2A is an internal multi-lumen tube. The internal multi-lumen tube is advantageous over the PA external luer systems that are used today simply because the external lures are just another component hanging off of an ET tube. Moreover, the hourglass shaped inflatable cuff 108 is envisioned to be disposed on either side of the patient's vocal cords providing improved comfort.

FIGS. 3A-3D illustratively depict an exploded view line drawing of a cap and the inlet body embodiment that collectively make up a cap arrangement consistent with embodiments of the present invention. With reference to the cap 300, the embodiment generally possesses a ventilation port 320 and an oxygen port 322. In this embodiment, the ventilation port 320 is essentially a ventilation tube defining a ventilation tube passageway (ventilator orifice) 338 and the oxygen port 322 is an oxygen inlet tube defining an oxygen inlet passageway 336, both tubes 320 and 322 extend radially from the intubation tube 102, as shown. The ET tube 102 is accessible through a probe port 310 sealed by a removable cap plug 312 when not being accessed. Certain embodiments envision the removable cap plug 312 made from rubber to seal the probe port 310 when engaged therewith. The removable cap plug 312 can further be tethered (not shown) to the cap 300 in order to eliminate the possibility of the removable cap plug 312 becoming lost when not covering the probe port 310. Certain embodiments envision a tether being a molded line on the cap 300 with the cap plug 312, a living hinge, a circular hinge that rotates the cap plug 312 out of the way, etc. The top surface 316 of the cap 300 further possesses a curved guide slot 318 arranged to cooperate with a detent pin 340 to lock the cap 300 in a rotational orientation, discussed later.

With reference to the inlet body 302, the ET tube 102 is fixedly connected thereto, such as by glue, ultrasonic welding or other techniques known to those skilled in the art. The main components of the inlet body 302, as shown from this perspective, include an inlet body port 308 that aligns with the probe port 310, a ventilation aperture 306, and a bite surface 304. The inlet body port 308 and the probe port 310 form part of the unobstructed ventilation passageway 101 leading into the tube inlet port 122.

Figure 3A:
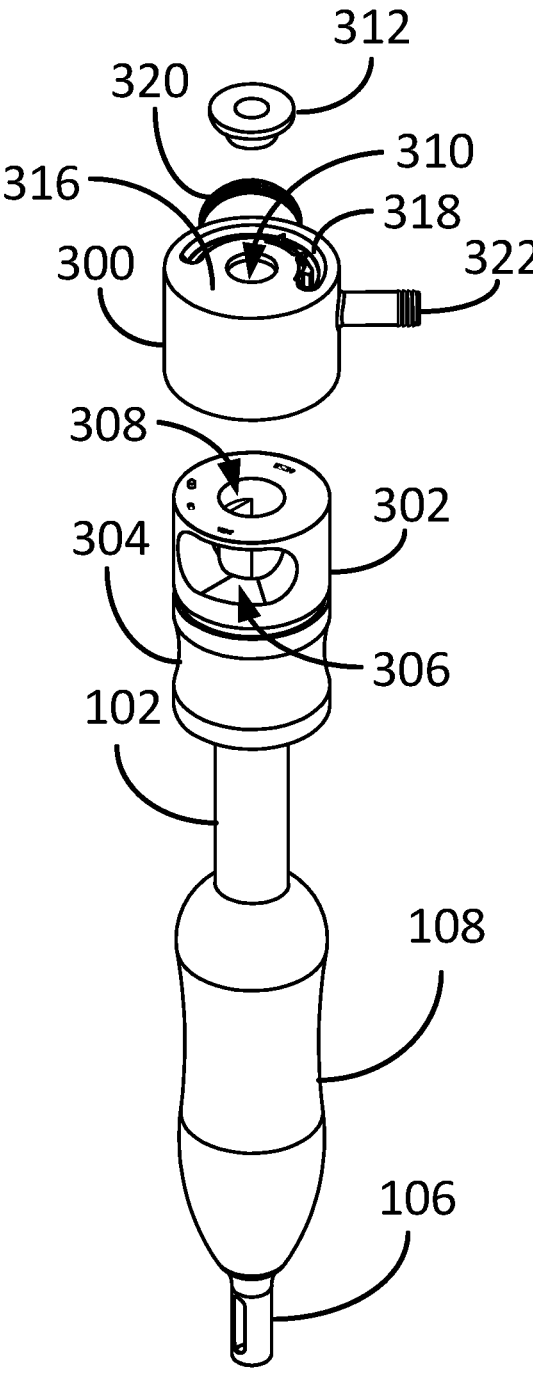
FIGS. 3A-3D illustratively depicts an exploded view line drawing of an embodiment of the cap 300 and the inlet body that collectively make up the cap arrangement consistent with embodiments of the present invention.
Figure 3B:
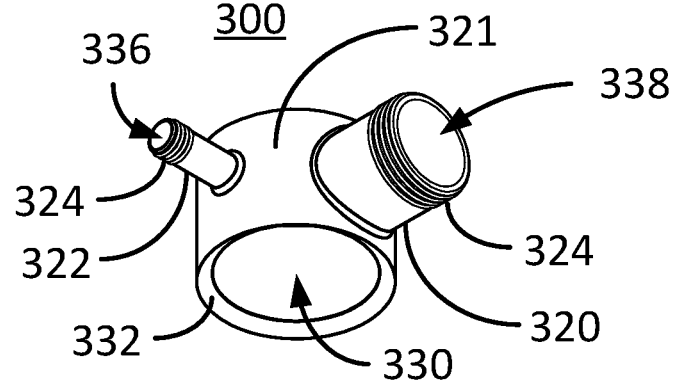

FIG. 3B is a line drawing of an isometric view of the cap 300 as seen from the bottom consistent with embodiments of the present invention. In the present embodiment, the ventilation port 320 generally comprises a tube with a ventilator orifice 338 as shown extending radially from the top side wall 321. The ventilation port 320 illustratively shows the ribbed/toothed port adapter 324, configured to receive a PVC tube (not shown) over the ribs 324, which locks or otherwise fixes the PVC tube in place and prevents it from sliding off the ventilation port 320. Likewise, the oxygen port 322 extends radially from the top side wall 321 and also possesses a ribbed port adapter 324 at the oxygen orifice 336. The cap 300 is configured to slidingly engage the inlet body 302 (in a conforming relationship that is by way of a conforming cavity 330) and to lock onto the inlet body 302 by way of an undercut lip 332 that snaps, or otherwise cooperates, with an inlet body groove 360. Slidingly engaged in this instance means that the cap 300 engages the inlet body 302 by sliding axially over the cylindrically shaped inlet body 302 until the cap 300 snaps in place on the inlet body 302 via the snap ring/lip 332. When snapped in place, the cap 300 is confined to only rotate on the inlet body 302. The undercut lip 332, when engaged with the inlet body groove 360, facilitates rotation of the cap 300 freely about the inlet body 302 to rotate the cap 300 in different positions over the inlet body 302. One skilled in the art will readily appreciate that other mechanical configurations can be used to retain the cap 300 onto the inlet body 302 while allowing free rotation about the inlet body 302 discussed in connection with FIGS. 4A-4C.

Figure 3C:
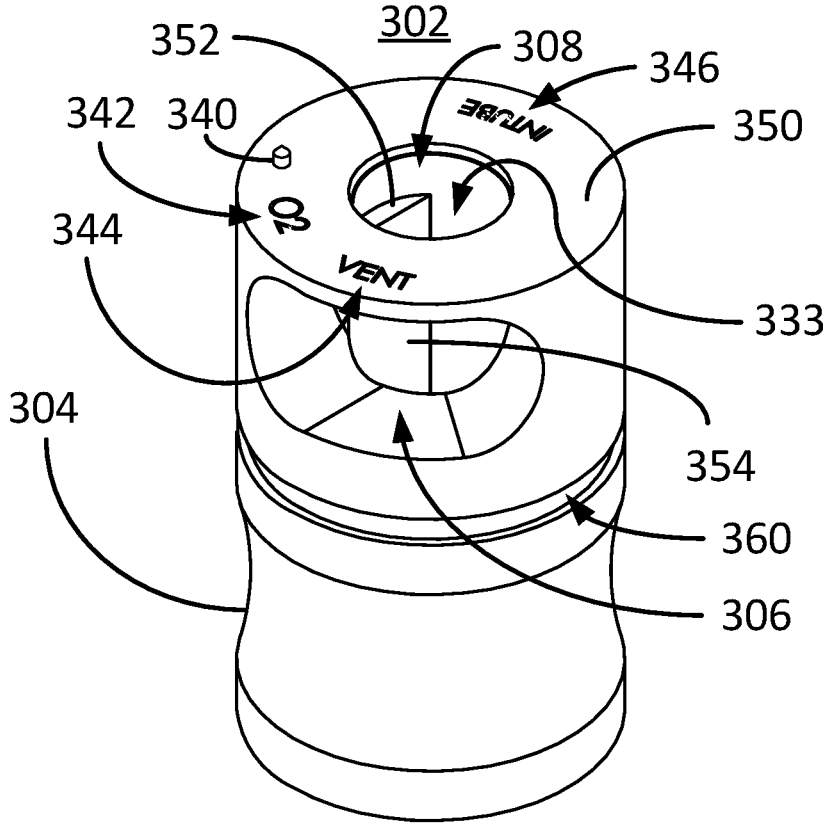

FIG. 3C is a line drawing of an isometric view of the inlet body 302 and described in view of elements from the earlier FIGS. In the present embodiment, the inlet body 302 shows a ventilation aperture 306 that leads into a hollow core 333. The inlet body 302 further shows the top 352 of the second pathway (cuff inflation pathway) 126 that mates with the ET tube 102 forming the contiguous second pathway 126 from the oxygen inlet passageway 336 to the cuff aperture 128. As shown through the inlet body port 308, the formed plenum 354 is sealed by a plenum cap 352, which prevents air from escaping from the second pathway 126 other than through the cuff aperture 128. With respect to the top inlet body surface 350, extending therefrom is the detent pin 340 configured to both guide and retain the cap 300 in rotational position when cooperating with the curved guide slot 318. Also, displayed on the top inlet body surface 350 are indicia as seen through the curved guide slot 318, which in this case are "INTUBE" 346, "O2" 342 and "VENT" 344. The indicia indicate when the cap 300 is in a rotational position when initially intubating a patient, in a second rotational position when providing oxygen to inflate the cuff 108, and in a third rotational position to ventilate the patient. Certain embodiments envision the inlet body 302 generally comprised of a unitary pliable material, such as a pliable PVC, rubber, or other polymeric material, etc. with the detent pin 340 being a rigid material. Other embodiments envision a top portion of the inlet body 302 being a rigid material such as a rigid polymer (or rigid compared with the pliable material used in inlet body 302), while the region including the bite surface 304 being composed of a pliable material. Other embodiments envision the bite surface 304 and the bite void 366 (of FIG. 3D) being stiff or somewhere between pliable and stiff. With this in mind, other configurations envision using a variety of different materials and manufacturing schemes to fit a desired outcome within the scope and spirit of the present invention.

Figure 3D:
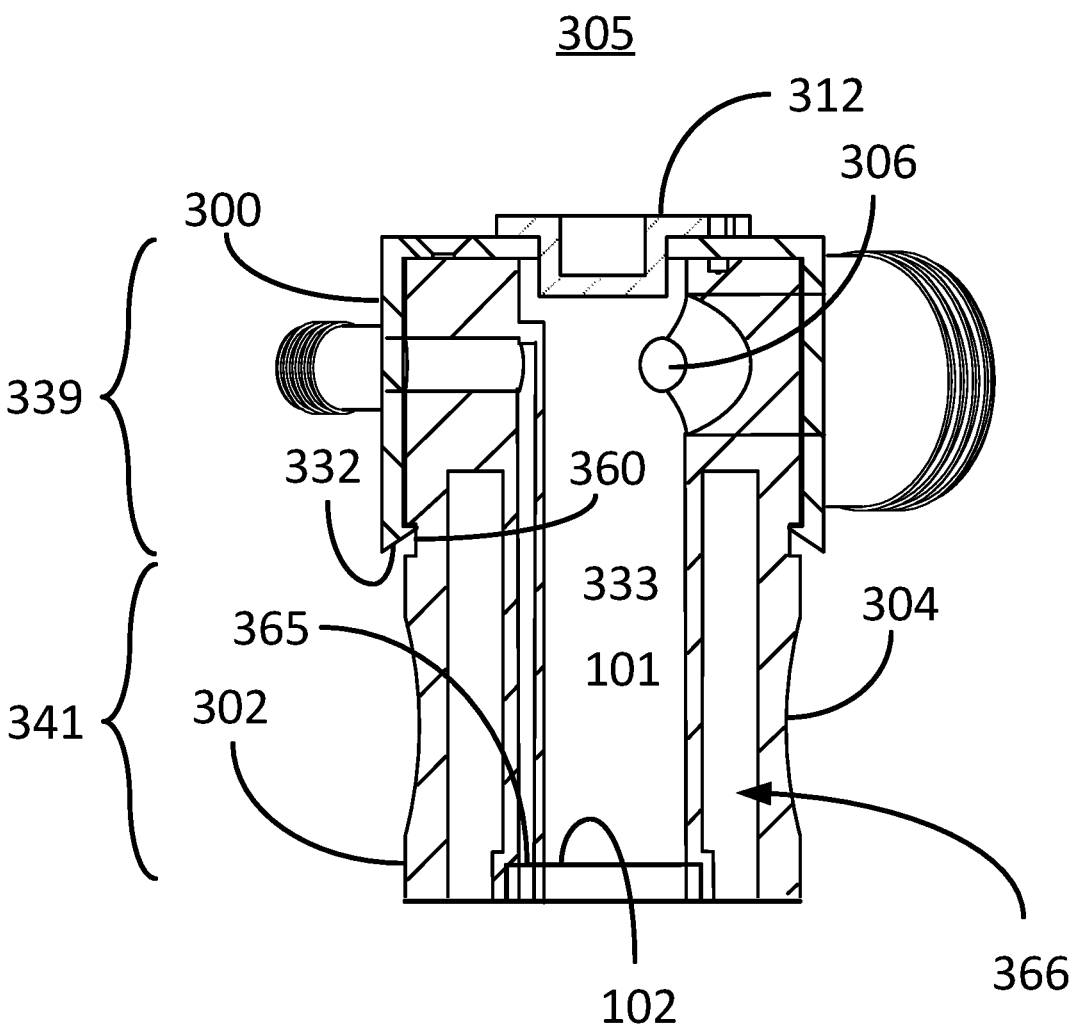

FIG. 3D is a cross-sectional side view line drawing of the cap body assembly 105 consistent with embodiments of the present invention. In this embodiment, the inlet body 302 is a unitary pliable material with a bite void 366 that facilitates compression of the bite surface 304 configured to collapse or conform to a patient biting down on the bite surface when the endotracheal tube apparatus 100 is deployed, or otherwise inserted, in a patient's trachea. The bite surface 304 is positioned to interface a patient's teeth. The endotracheal tube interface 365 shows where the ET tube 102 is fixedly attached to the inlet body 302, wherein the hollow core 333 of the cylindrically shaped inlet body 302 forms the continuous ventilation passageway 101 in the ET tube 102. As previously discussed, the undercut lip 332 of the cap 300 snaps into the inlet body groove 360 in an engaging relationship. In this configuration, when assembled, the undercut lip 332 is configured to deflect outwardly from the cylindrically shaped inlet body 302 while the cap 300 is slid over an upper portion 339 of the inlet body 302 until the undercut lip 330 springs back, or otherwise snaps, into the groove 360. Once the cap 300 is rotationally engaged in a cooperating relationship with the inlet body 302, the cap 300 is retained on the inlet body 302 in the vertical direction but is free to rotate about the cylindrically shaped inlet body 302. When rotationally engaged, the cap 300 covers the upper portion 339 of the inlet body 302, which includes the cuff inflation aperture 307 (of FIG. 4B) in the ventilation aperture 306. For reference, the lower portion 341 includes the bite void 366 and is not covered by the cap 300.

FIGS. 4A and 4B are line drawings of a cross-section of a cap body assembly consistent with embodiments of the present invention. As shown in FIG. 4A, the cross-section line 402 passes through the center of ventilator port 320. In this configuration, the detent pin 340 is locked against the ventilator detent 405, as shown by the indicator arrow 404 pointing to "VENT". In FIG. 4B, the cross-section 402 of the ventilator port 320 reveals the ventilation aperture 306 by way of the ventilator orifice 338. Because part of the cap 300 is cut away, the cuff inflation aperture 307 shows where the oxygen port 322 leads. In this embodiment, when the indicator arrow 404 is pointing to the "VENT", the "O2" is also open to continuously provide oxygen to the inflatable cuff 108 at a constant pressure to keep (or maintain) the inflatable cuff 108 inflated. For reference, the detent pin 340 is shown standing proud on the top inlet body surface 350.

Figure 5A:
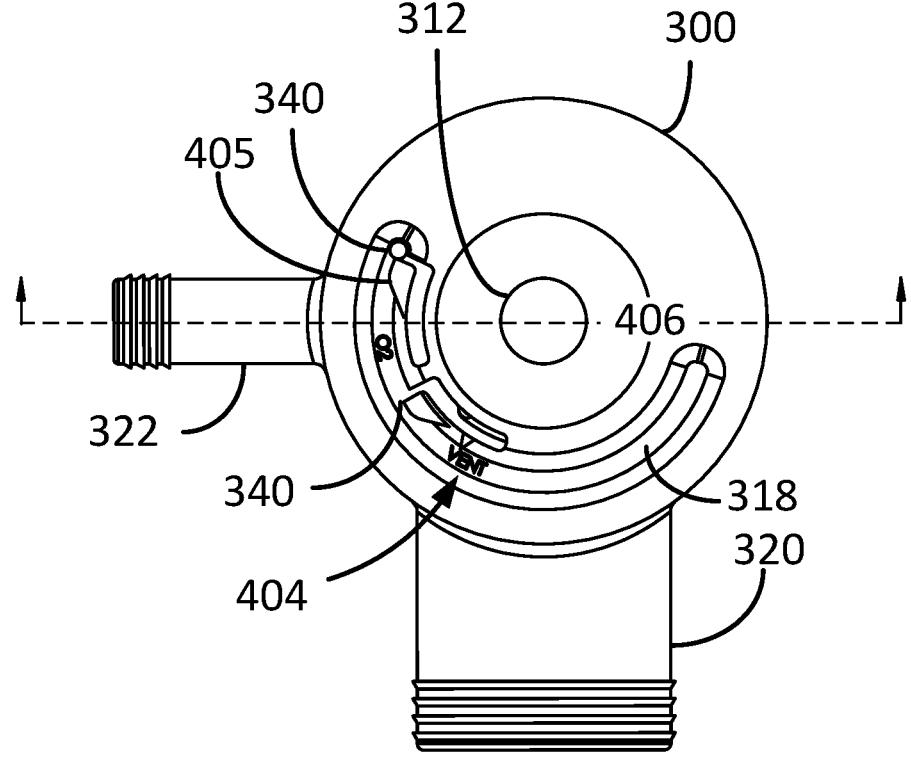
FIGS. 5A-5B are line drawings of a cross-section of a cap body assembly embodiment in the same orientation as FIGS. 4A and 4B consistent with embodiments of the present invention.
Figure 5B:
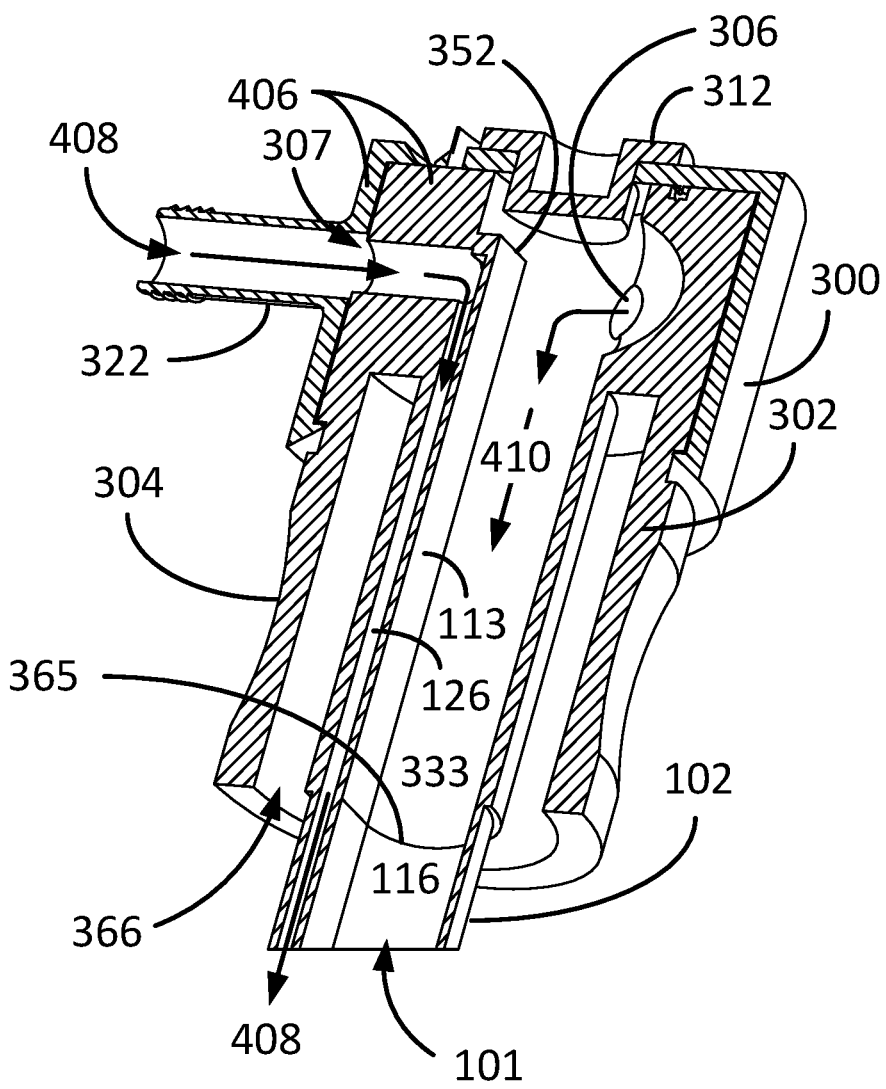

FIGS. 5A-5B are line drawings of a cross-section of a cap body assembly 105 embodiment in the same cap assembly 105 rotational orientation as FIGS. 4A and 4B. As shown in FIG. 5A, the cross-section line 406 cuts through the center of oxygen port 322. In this configuration, the detent pin 340 is locked against the ventilator detent 405 as indicated by the indicator arrow 404 pointing to "VENT". In FIG. 5B, the cross-section 406 illustratively depicts the oxygen port 322 cut away to show the cuff inflation aperture 307 leading into the second endotracheal tube pathway 126, which is formed by a channel between the inside of the ET tube 102 and the second pathway plenum wall 113. As shown by the arrows 408, in this configuration, oxygen is supplied to a second endotracheal tube pathway 126 by an oxygen source, which feeds the inflatable cuff 108 keeping it inflated while the patient is being ventilated 410. As will be appreciated by a skilled artisan, ventilation forces air 410 into the lungs of the patient and allows the air to flow back out through the ventilation aperture 306 and out the ventilator port 320 of FIG. 5A. For reference, the bite void 366 is shown surrounding the first (ventilation) and second pathways 101 and 126, respectively. The proximal endotracheal tube end 116 is adapted and arranged to mate 365 with the cap arrangement 105 whereby the hollow core 333 of the cylindrically shaped inlet body 302 aligns with uninterrupted ventilation pathway 101 in the ET tube 102. The endotracheal tube interface 365 shows where the ET tube 102 is fixedly attached to the inlet body 302. Also, the removable cap plug 312 is depicted blocking the probe port 310 (covered by the cap plug 312).

Figure 6A:
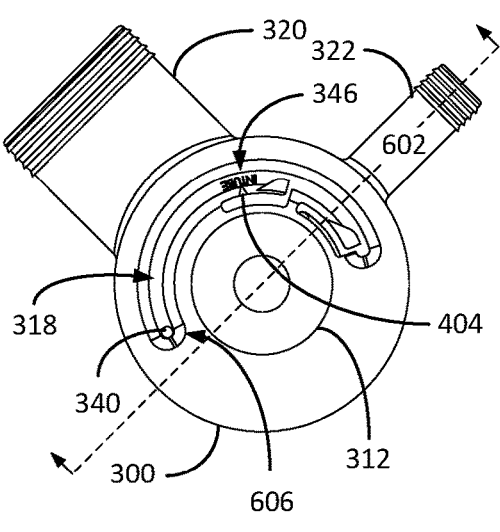
FIGS. 6A-6B illustratively depict cross-section line drawings of an embodiment of the endotracheal tube apparatus with the cap rotated in an intubation setting consistent with embodiments of the present invention.
Figure 6B:
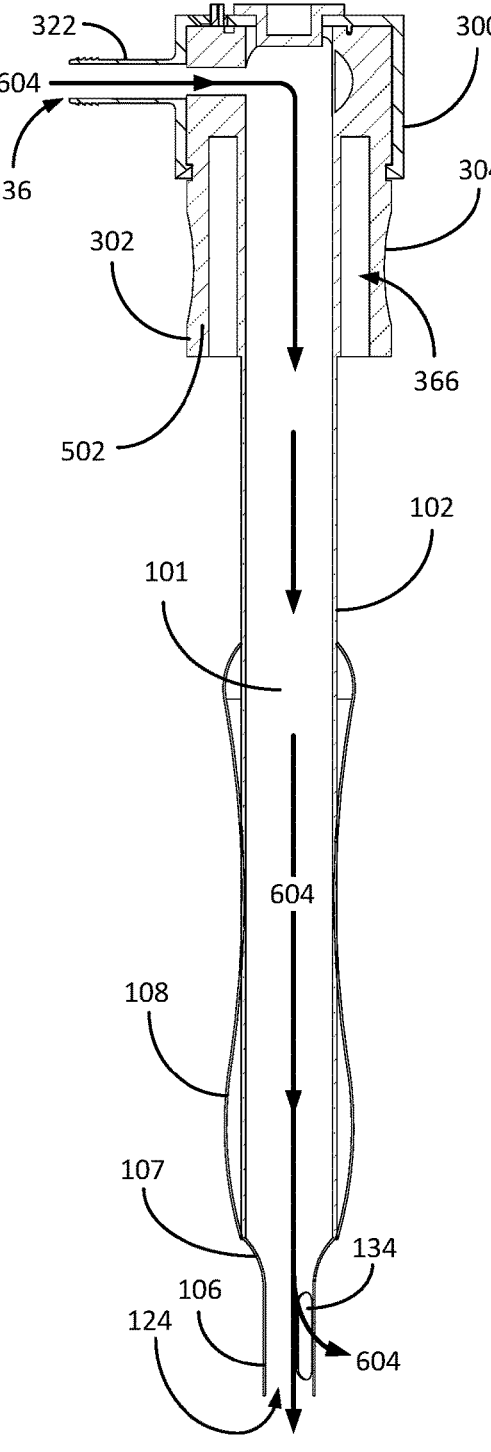

FIGS. 6A-6B illustratively depict cross-section line drawings of an embodiment of the ET tube apparatus 100 with the cap 300 rotated in an intubation setting consistent with embodiments of the present invention. As shown in FIG. 6A, the cap 300 is rotated to the "INTUB", or intubation, setting 346 as indicated by the indicator arrow 404 wherein the detent pin 340 is at the stop position 606 at the edge of the curved guide slot 318. This is the initial position of the cap 300 from the time when a caregiver is about to intubate a patient to when the caregiver has completed deploying the intubation tube 102 into the patient. FIG. 6B shows a cross-section of the ET tube apparatus 100 along the cross-sectional cut line 602 (as shown in FIG. 6A). When the cap 300 is in the intubation position, the oxygen inlet tube 322 (and therefore the oxygen inlet passageway 336) is in line with the ventilation aperture 306. Hence, oxygen flows 604 under pressure into the oxygen port 322, through the flexible hollow ET tube 102 and out the distal tip outlet port 124 and the at least one distal tip side port 134. When a patient is intubated in this way, oxygen can feed their lungs while the intubation tube is being inserted, which advantageously reduces the time a patient is deprived of oxygen. As further shown, the inflatable cuff 108 is in a deflated state so that the intubation tube 102 can be threaded past a patient's vocal cords (not shown) without obstruction. Once the endotracheal tube apparatus 100 is deployed in the proper position, the inflatable cuff 108 is inflated at the patient's vocal cords.

Figure 7C:
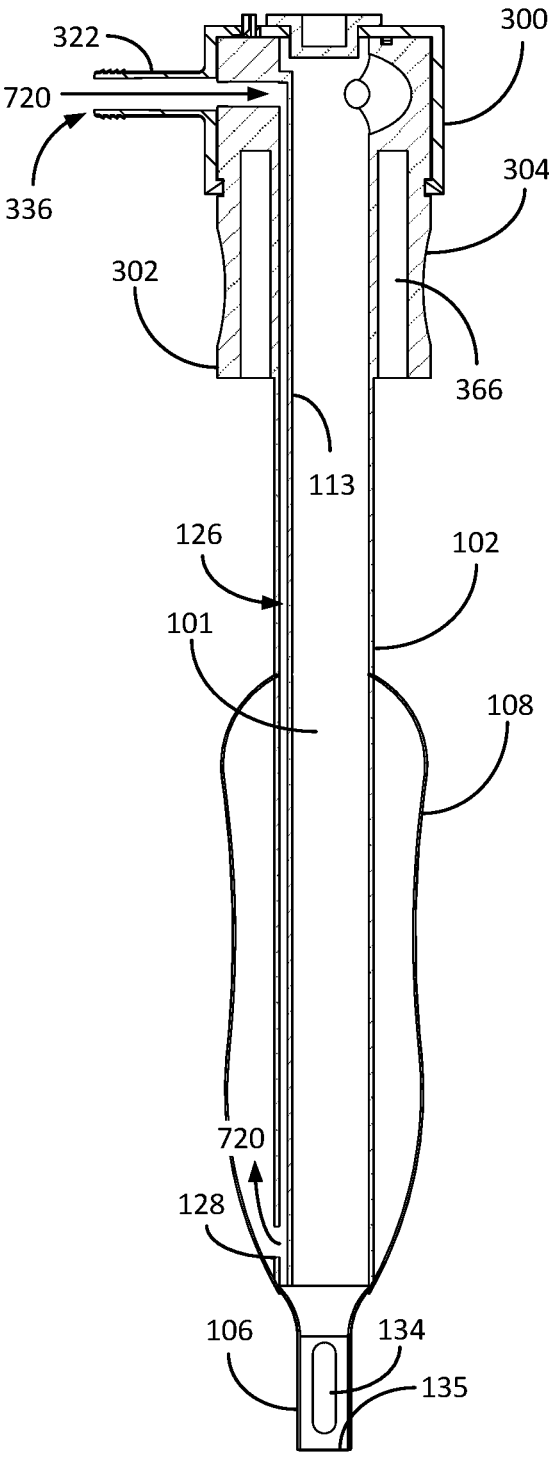

FIGS. 7A-7C are line drawings illustratively depicting ET tube apparatus 100 with the cap rotated in the O2 cuff setting consistent with embodiments of the present invention. As shown in FIG. 7A, the cap 300 is in the process of being rotated to the "O2", or oxygen, setting 342 as indicated by the indicator arrow 404, wherein the detent pin 340 is deflecting the first tab 702 as it traverses the curved guide slot 318. The first tab 702 is at the distal end of a cantilever arm 704. The cantilever arm 704 is shown by hashed lines for clarity. The cantilever arm 704 is physically deflected (elastically) by the detent pin 340 sliding up against a ramp on the first tab 702 when the cap 300 is turned (rotated) counterclockwise 712 by hand when moving the indicator arrow 404 to the O2 setting 342. When the operator (or whomever is setting the cap 300) rotates the cap 300 so that the detent pin 340 is just past the first tab 702, the cantilever 704 elastically springs back into its non-deflected position thereby retaining the detent pin 340 against the detent 706 of the first tab 702. This is depicted in FIG. 7B. The detent 706 servers as a stop face/surface to prevent the detent pin 340 from sliding in the curved guide slot 318 towards the starting point (the INTUB location).

As shown in FIG. 7C, with the cap 300 rotated to the O2 setting 342, oxygen is infused 720 into the inflatable cuff 108 causing it to inflate. More specifically, when the cap 300 is in the second rotational position (i.e., the O2 setting of FIG. 7B in this example) the oxygen inlet passageway 336 is aligned (in line) with the cuff inflation aperture 307 (of FIG. 5B), meaning there is communication between the oxygen inlet passageway 336 and the plenum pathway 126. Accordingly, as shown by the arrow 720, when the cap 300 is positioned to the O2 setting on the inlet body 302, an unobstructed pathway for air to flow through the oxygen port 322 is created. Air flows down the plenum pathway 126 (formed by the inner wall 113), out of the cuff port 128, and into the inflatable cuff 108. O2 is infused into the oxygen port 322 by way of a pressurized oxygen source (e.g., an oxygen tank or central oxygen line, to name a few sources), via a tube (shown in FIG. 9) that is connected to the oxygen port 322. In this way, the inflatable cuff 108 inflates thereby conforming and sealing the endotracheal tube apparatus 100 inside the vocal cord space to a) hold the endotracheal tube apparatus 100 in place and b) prevent regurgitation from entering the patient's lungs. Certain embodiments envision the oxygen enriched air provided through the oxygen port 322 not going into the ventilation passageway 101.

Figure 8A:
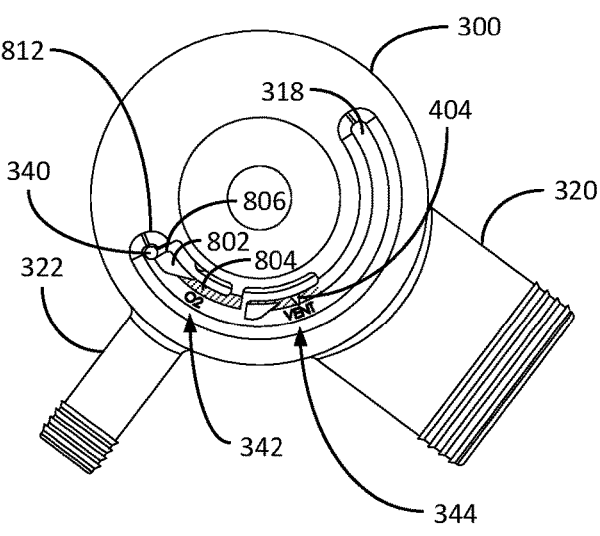
FIGS. 8A and 8B illustratively depict line drawings of the endotracheal tube apparatus embodiment with the cap rotated in the ventilation setting consistent with embodiments of the present invention.
Figure 8B:
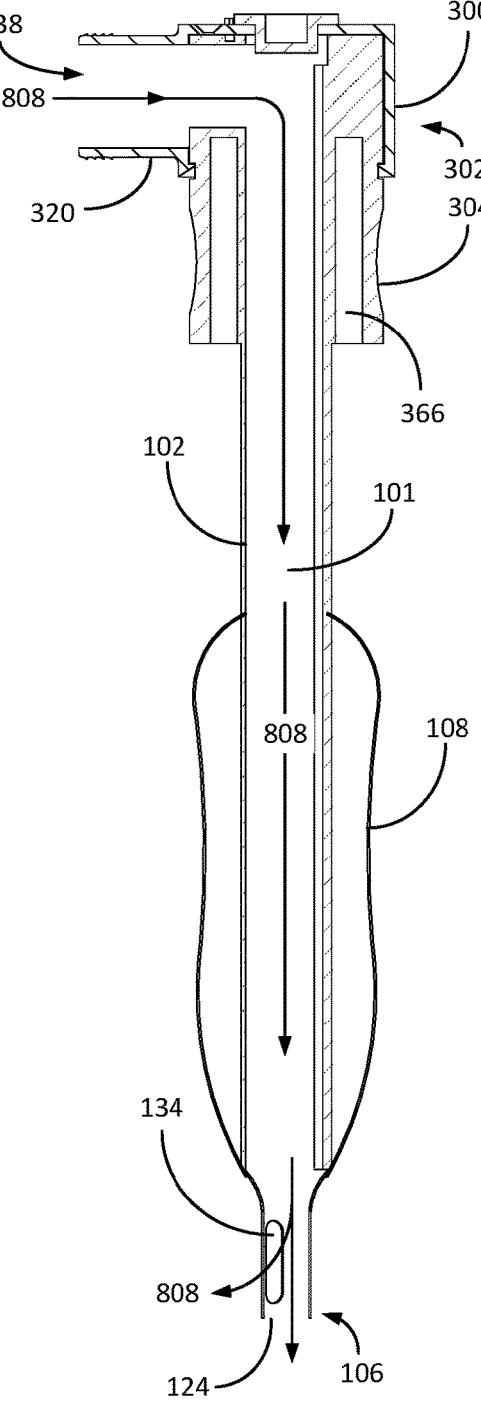

FIGS. 8A and 8B illustratively depict line drawings of the ET tube apparatus 100 with the cap 300 rotated to the ventilation setting consistent with embodiments of the present invention. As shown in FIG. 8A, the cap 300 is rotated so that the indicator arrow 404 points to the "VENT", or ventilation, setting 344 wherein the detent pin 340 becomes locked against the detent 806 of the second tab 802. The second tab 802, which is disposed at the end of a second cantilever 804, is physically deflected when the detent pin 340 traverses to the end of the guide slot 812 when the cap 300 is turned (rotated by hand) counterclockwise 712 to the VENT setting 344 (shown by the arrow in FIG. 7A). The detent 802 servers as a stop face/surface to prevent the detent pin 340 from sliding in the curved guide slot (channel) 318 towards O2 342 setting and INTUB location 346 (hidden under the cap 300 opposite the "VENT" setting 344).

As shown in FIG. 8B, with the cap 300 rotated to a third rotational position (the VENT setting 342 in this example), ventilation tube passageway 338 is aligned (in line) with the ventilation aperture 306 (of FIG. 3D), meaning there is communication between the ventilation tube passageway 338 and the ventilation passageway 101 (the second pathway). Accordingly, as shown by the arrow 808, when the cap 300 is positioned to the VENT setting 342 on the inlet body 302, an unobstructed pathway for air to flow through the oxygen port 322 is created. Ventilation air is infused into the ventilation port 320 by way of a ventilator for example, via a tube (shown in FIG. 9) that is connected to the ventilation port 320, down the unobstructed ventilation pathway 101 and out the tip 106 (distal tip outlet port 124 and the at least one distal tip side port 134). In this way, the appropriate air and oxygen mixture is ventilated into the patient's lungs and the exhalent is moved out from the patient's lungs.

Certain embodiments envision that the inflatable cuff 108 is adapted to receive air throughout the period of time that the endotracheal tube 100 is deployed in a patient (i.e., throughout the time that the patient is intubated, which could be weeks) to keep the inflatable cuff 108 from deflating. In this scenario, a one-way valve can be employed along the second/cuff pathway, e.g., the oxygen port 322, and/or at the cuff port 128, and/or somewhere along the cuff pathway 126. Other embodiments envision the cuff 108 being capable of holding the infused air without leaking until intentionally being deflated. In this alternative embodiment, the oxygen port 322 is not aligned with the cuff inflation aperture 307 but rather is blocked by the side wall 321.

Figure 9:
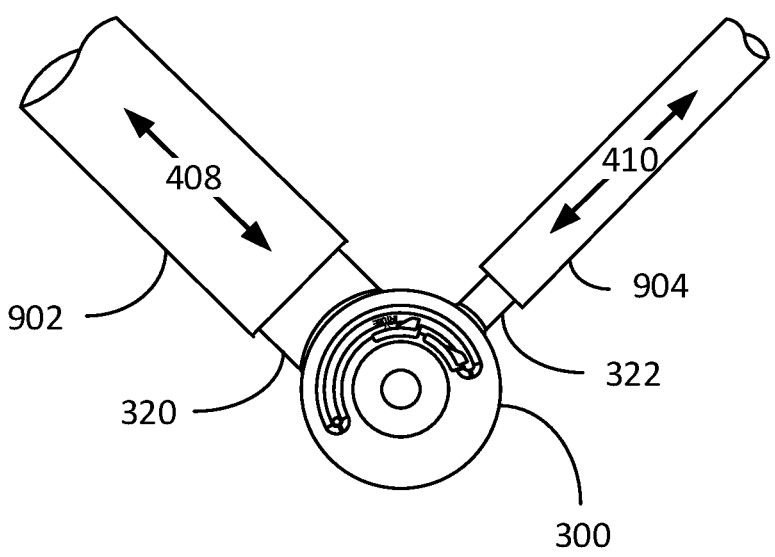
FIG. 9 illustratively depicts a line drawing of a top view of an endotracheal tube apparatus embodiment connected to a ventilation line and an enriched oxygen line consistent with embodiments of the present invention.

FIG. 9 illustratively depicts a line drawing of a top view of an ET tube apparatus embodiment 100 connected to a ventilation line and an enriched oxygen line consistent with embodiments of the present invention. More specifically, a ventilation line 902 connects the ventilation port 320 with a ventilator (not shown), which serves as an air source (i.e., ambient air or something other) depicted in the top view of the cap 300. In one embodiment, the ventilator line 902 is a flexible PVC tube that is pressure fitted over ribbed/toothed port adapters 324 at the distal end of the ventilation port 320, as shown in FIG. 3B. Similarly, the enriched oxygen line 904 connects an enriched oxygen source (such as an oxygen tank or in wall oxygen system, for example) with the oxygen port 322. In one embodiment, the enriched oxygen line 904 is a flexible PVC tube that is pressure fit over the ribbed/toothed port adapters 324 at the distal end of the oxygen port as shown in FIG. 3B. The ribbed/toothed port adapter 324 mechanically locks the flexible ventilator line 902 and the enriched oxygen line 904 in place.

Figure 10A:
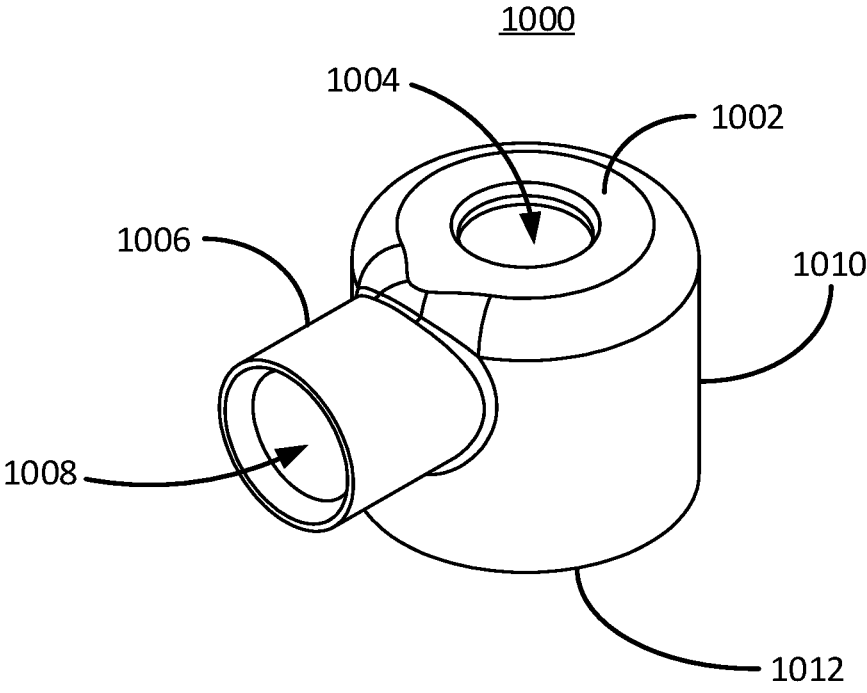
FIGS. 10A-10D illustratively depict line drawings of an optional endotracheal tube cap embodiment consistent with embodiments of the present invention.

FIGS. 10A-10D illustratively depict line drawings of an optional ET tube cap embodiment consistent with embodiments of the present invention. In the present embodiment, the ET tube cap 1000 is envisioned as a unitary cap with an oxygen intake tube 1006. In more detail as shown in FIG. 10A, the ET tube cap 1000 is essentially a cylindrically shaped cap housing 1010, defining a cap top 1002 and a cap base 1012, with an oxygen intake tube 1006 extending radially from the cap housing 1010. The oxygen intake tube 1006 distally terminates to an oxygen intake port 1008, which serves as an opening into the endotracheal tube cap 1000. In the embodiment shown, the cap top 1002 possesses a probe port 1004 configured to provide access for a camera, an endoscope, a guide wire, or some other device that could be placed in the cap 1000 or in the ET tube 1016 (of FIG. 10D). The probe port 1004 is configured to be covered by a cap plug 312 (shown in FIG. 10D). Certain other embodiments envision a solid cap top 1002 with no probe port 1004. Some embodiments envision the endotracheal tube cap 1000 being a unitary rigid element that can be molded out of plastic or other materials known to those skilled in the art. Other embodiments envision the ET tube cap 1000 made of a pliable material such as rubber of varying stiffness/durometers.

Figure 10B:
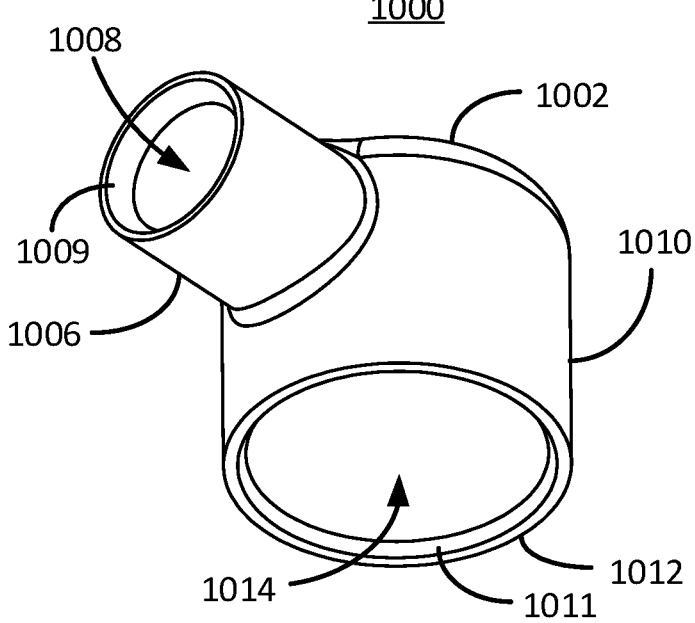

FIG. 10B is a line drawing of an isometric underside view of the ET tube cap 1000 consistent with embodiments of the present invention. FIG. 10B is in view of FIGS. 10A, 10C and 10D. From this vantage, the hollow core 1014 primarily comprises the inside of the cylindrically shaped cap housing 1010 as shown through the ET tube aperture 1014 at the cap base 1012. The ET tube aperture 1014 is configured to receive the top end of an endotracheal tube 1016. The housing 1010 possesses a chamfered edge 1011 at the endotracheal tube aperture 1014 that increases the endotracheal tube aperture diameter to at least 5% larger than the outer diameter 1017 of the endotracheal tube 1016. The oxygen intake port 1008 possesses an intake chamfer 1009 that increases the oxygen intake port diameter 1021 to at least 5% larger than the outer diameter 1019 of the oxygen intake tube 1006. The oxygen intake port 1008 is in communication with the inner bore/intake pathway inside of the intake tube 1006, which is in communication with the hollow core 1015, which is in communication with the endotracheal tube aperture 1014 (these components 1008, 1006, 1015 and 1014 form a continuous and uninterrupted pathway).

Figure 10C:
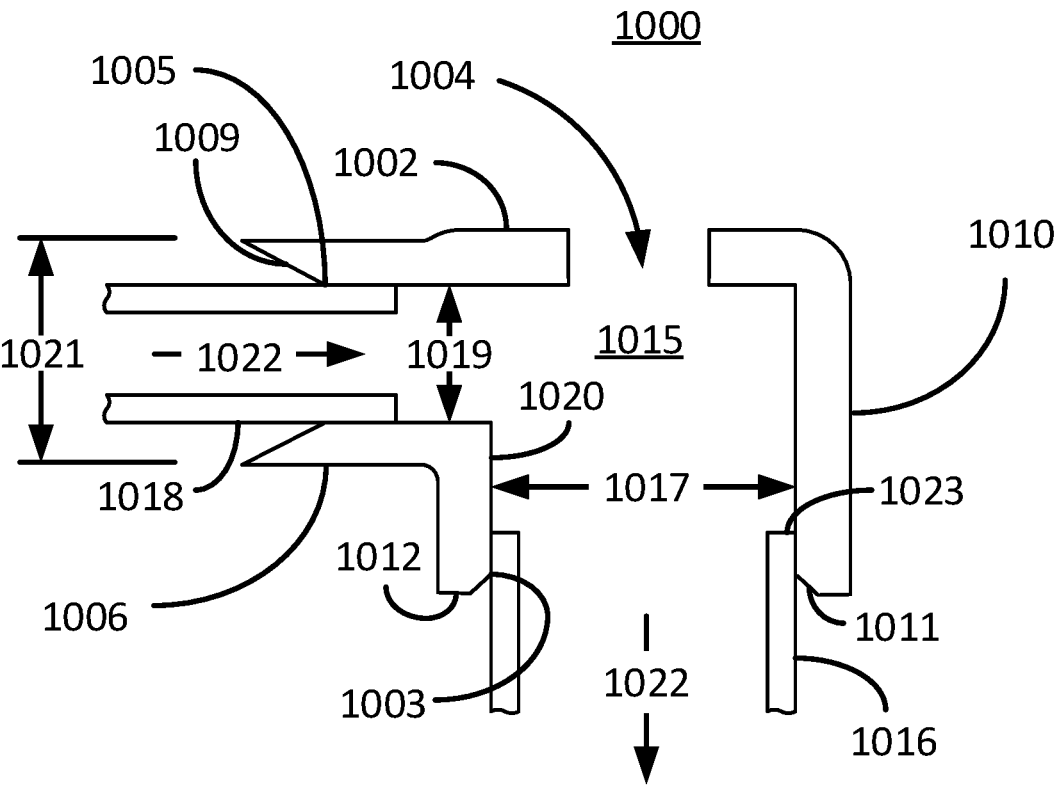

FIG. 10C (in view FIGS. 10A, 10B and 10D) illustratively depicts line drawing of a side view cross-section of the ET tube cap 1000 with an ET tube 1016 and oxygen source tube 1018 consistent with embodiments of the present invention. As shown, the ET tube cap 1000 comprises the hollow core 1015 inside of the cylindrically shaped cap housing 1010 wherein the housing 1010 defines the cap top 1002 and the cap base 1012. The oxygen intake tube 1006 extends from the cap housing 1010 in a radial direction with reference to the cylindrical housing 1010. The oxygen intake tube 1006 terminates in an oxygen intake port 1008, which is configured to cooperate with an oxygen source tube 1018. The intake chamfer 1009 increases the oxygen intake port diameter 1021 to accommodate funneling the oxygen source tube 1018 into the oxygen intake tube 1006 quickly in a snug/tightly conforming relationship with the inner diameter 1019 of the oxygen intake tube 1006. Accordingly, an oxygen source tube 1018 can be quickly pressed into the oxygen intake tube 1006 in preparation for intubating a patient. In this embodiment, the oxygen source tube 1018 is disposed, or pressed, in the oxygen intake tube 1006 beyond where the intake chamfer 1009 ends/transitions 1005 to a consistent diameter bore 1019. Also in this embodiment, the ET tube 1016 is disposed, or pressed, in the inner bore 1020 of the hollow core 1015 beyond where the chamfered edge 1011 ends/transitions 1003.

With continued reference to the cylindrically shaped cap housing 1010, the hollow core 1015 extends through the ET tube aperture 1014 at the cap base 1012. The ET tube aperture 1014 is configured to receive the proximal end 1023 of an ET tube 1016. The housing 1010 possesses a chamfered edge 1011 at the ET tube aperture 1014 that increases the ET tube aperture 1014 to at least 5% larger than the outer diameter of the ET tube 1016. The chamfered edge 1011 increases the ET tube aperture 1014 to accommodate funneling the ET tube 1016 quickly into the hollow core 1015 in a snug/tightly conforming relationship with the inner housing surface 1020 of the hollow core 1015. In this way, an ET tube 1016 can be quickly pressed into the hollow core 1015 through the base side 1012 in preparation for intubating a patient in an emergency. As can be appreciated, with the oxygen source tube 1018 and ET tube 1016 attached to the ET tube cap 1000, enriched oxygen can flow through the oxygen source tube 1018 (from an oxygen source such as an oxygen tank), through the uninterrupted oxygen pathway 1022, through the ET tube 1016 and out the ET tube exit port (not shown). In this way, a patient is infused with oxygen while being intubated.

Figure 10D:
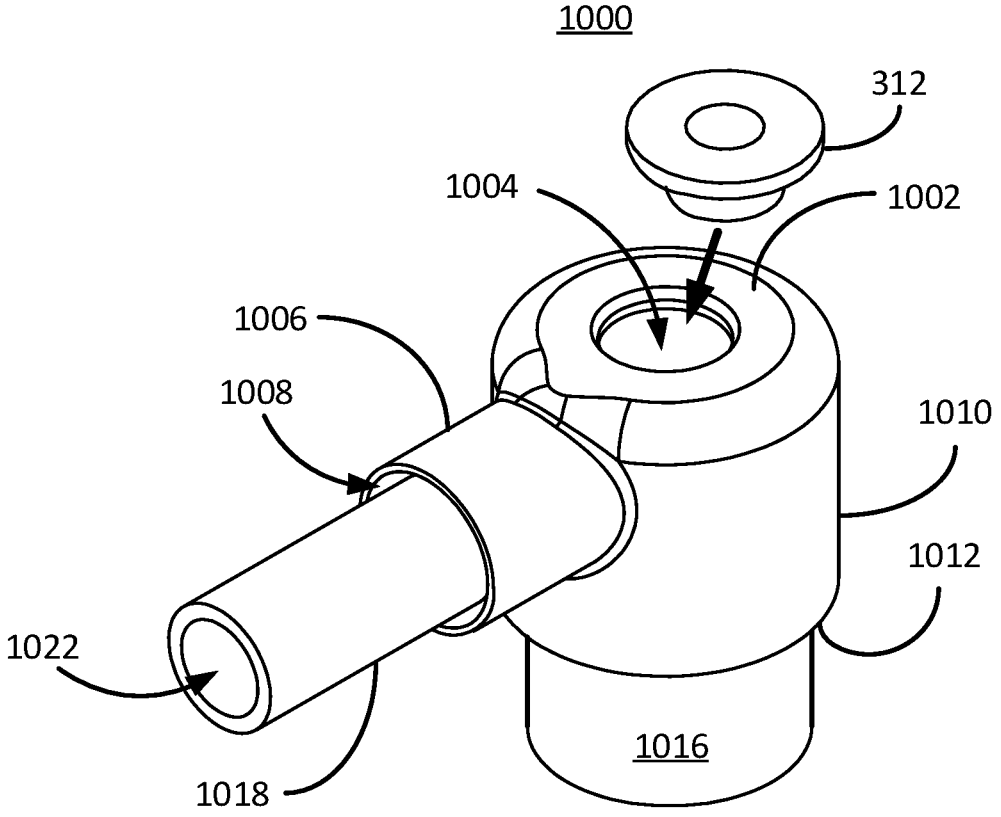

FIG. 10D (in view of FIGS. 10A-10C) is a line drawing of an isometric view of the ET tube cap 1000 connected with an oxygen source tube 1018 and an ET tube 1016 consistent with embodiments of the present invention. As shown, the oxygen source tube 1018 connects in a tightly conforming relationship inside of the oxygen intake tube 1006. The chamfered edge 1009 makes the diameter 1021 of the oxygen intake port 1008 larger than the outer diameter 1019 of the oxygen source tube 1018. The ET tube 1016 is shown fixedly extending from the cap base 1012. Also shown is a cap plug 312 configured to cover the probe port 1004 extending through the cap top 1002 and into the hollow core 1015. The cap plug 312 is envision to seal off the hollow core 1015 from the outside/exterior environment as essentially a "closed system" wherein the only ways to access the hollow core 1015 are by way of the oxygen intake port 1008 and the ET tube aperture 1014. The outside/exterior environment is an environment outside of the oxygen source tube 1018 and the ET tube 1016 when they are connected with the ET tube cap 1000, such as an operating room or open air. Other embodiments envision the cap top 1002 without a probe port 1004. In this embodiment, the only ways to access the hollow core 1015 are by way of the oxygen intake port 1008 and the ET tube aperture 1014. For reference, an ET tube 1016 is an open system without the ET tube cap 1000 because the proximal end 1023 of the endotracheal tube 1016 is open to the environment.

Certain embodiments envision a method of intubating a patient with enriched oxygen assistance, using an embodiment of the endotracheal tube cap 1000. In an emergency when a patient needs immediate intubation, certain embodiments envision removing an endotracheal tube cap 1000 from a package. Next, manually pressing an oxygen source tube 1018 into the oxygen intake port 1008 in a closely conforming relationship (i.e., snuggly fitting) inside of the oxygen intake port 1008. Snuggly fitting is considered providing essentially an airtight to substantially airtight connection, which can include a small amount of leakage with the majority of the enriched oxygen passing through the ET tube cap 1000. This can be accomplished by manually pressing the proximal end 1023 of an ET tube 1016 through the endotracheal tube aperture 1012 and into the hollow core 1015 in a closely conforming relationship inside of the hollow core 1015 (essentially airtight to substantially airtight). Substantially airtight means only a small/insignificant amount of leakage of enriched oxygen with the majority of the enriched oxygen passing from the endotracheal tube cap 1000 through and out of the ET tube 1016. The chamfered edge 1009 at the oxygen intake port 1008 facilitates the ability to quickly press the oxygen source tube 1018 into the oxygen intake tube 1006. The chamfered edge 1011 at the ET tube aperture 1014 facilitates the ET tube 1016 into the hollow core 1015 via the ET tube aperture 1014. Next, an oxygen source provides flowing enriched oxygen through the oxygen source tube 1018, then (the enriched oxygen) through the oxygen intake tube 1006 via the oxygen intake port 1008, then through the hollow core 1015, then through the ET tube aperture 1014, and out of a distal aperture (not shown) in the ET tube 1016. With the enriched oxygen flowing out through the distal end (not shown) of the ET tube 1016, a next step is to insert the ET tube 1016 into a trachea thereby oxygenating a patient while being intubated. Once the ET tube 1016 is fully inserted into the patient's trachea, the ET tube cap 1000 can be removed from the proximal end 1023 of the ET tube 1016 (i.e., the cap 1000 can be pulled off and discarded). With the ET tube 1016 now an open system, the ET tube 1016 can be connected with a ventilation tube 902 that is already connected or can be connected to a ventilator (not shown) to assist a patient's breathing.

Figure 11A:
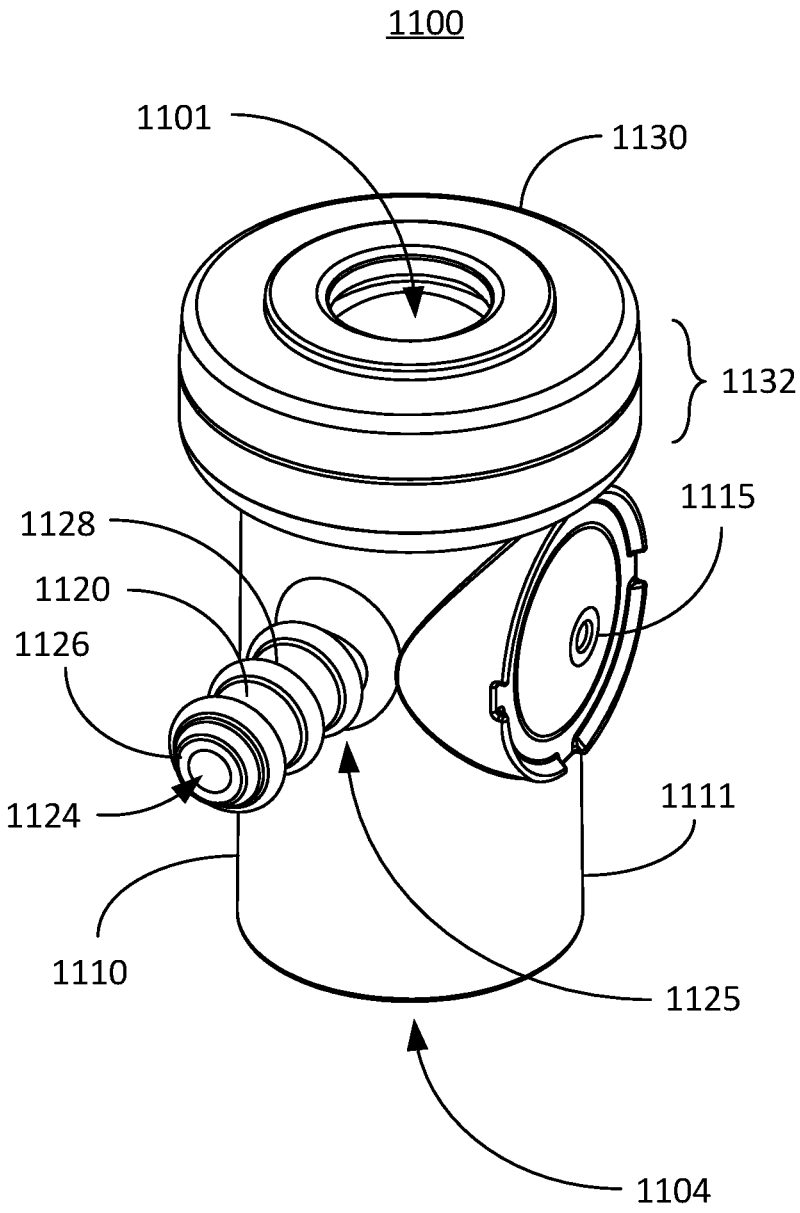
FIGS. 11A-11E are line drawings of another optional endotracheal tube cap embodiment consistent with embodiments of the present invention.

FIG. 11A is an isometric view of a simple ET oxygen cap embodiment consistent with embodiments of the present invention. As shown here, the ET oxygen cap 1100 generally comprises a tubular housing 1110 that is defined between a cap top 1130 and an ET tube receiving aperture 1104. Certain embodiments envision the tubular housing 1110 being made/constructed from a polymer material, such as PVC, nylon, etc. Other embodiments envision the majority of the ET oxygen cap 1100 being made from the same material. An intake tube 1120 extends at 90° from the outer side wall 1111 of the tubular housing 1110. The intake tube 1120 is envisioned to connect to an oxygen tank, or other oxygen source, via an oxygen tube. The intake tube 1120 is connected to the tubular housing 1110 at a proximal tube end 1125 and extends outwardly terminating at a distal tube end 1126. The intake tube 1120 comprises a plurality of push connect ring fittings 1128 (such as barbed fittings or ring fittings) that help retain a flexible tube on the outer surface of the intake tube 1120. Also shown is the distal intake tube port 1124 where oxygen is made to flow into the tubular housing 1110. A pressure relief valve 1115 is also located on the outer housing sidewall 1111 at 90° from the intake tube 1120. However, the pressure relief valve 1115 can reside in other locations along the outer housing sidewall 1111, or optionally, at the cap top 1130.

The present embodiment includes an instrument port 1101 (located at the cap top 1130) that accommodates a stylet, a bronchial scope, or the like. This instrument port embodiment 1101 is accompanied with an instrument housing backup seal valve 1102 and a cross-slit valve 1106 disposed inside of an instrument port housing 1132. However, other embodiments do not include an instrument port 1101. The ET oxygen cap 1100 is not intended to be connected to a ventilator, which assists breathing for a distressed person.

Figure 11B:
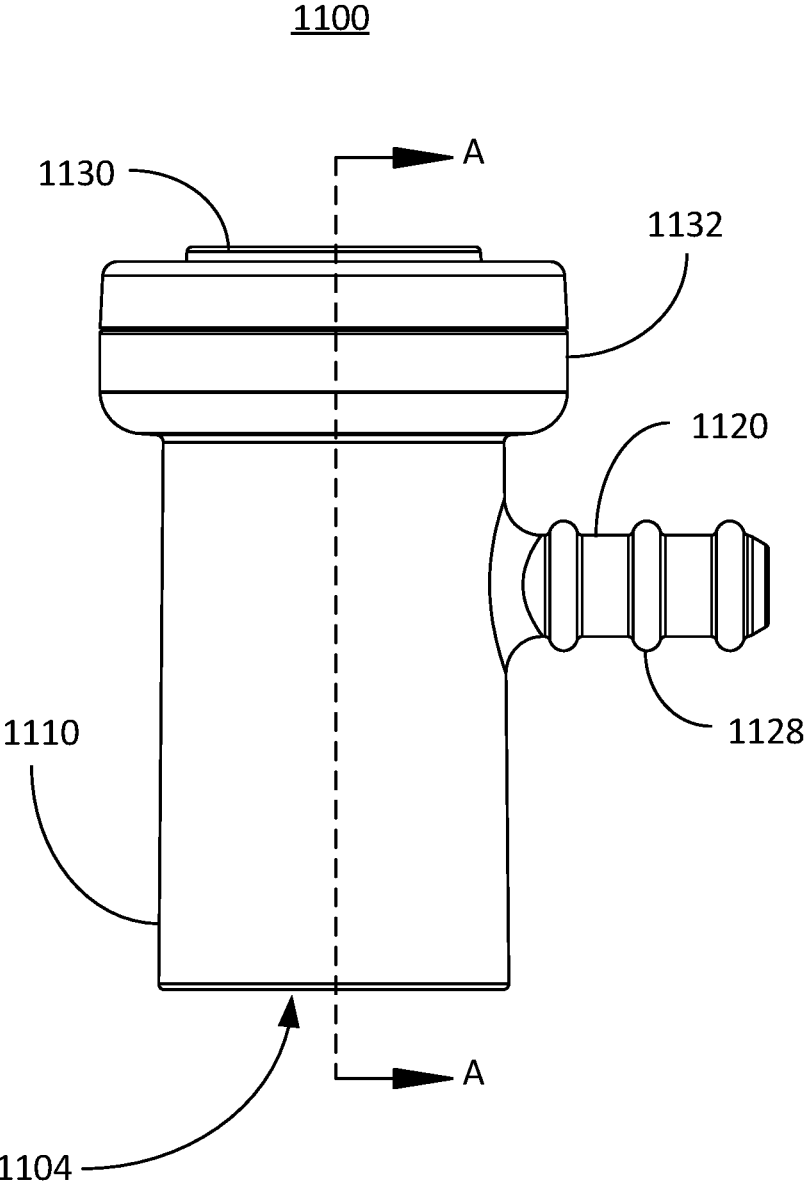

FIG. 11B is a side view line drawing of the ET oxygen cap 1100. As shown, the intake tube 1120 is extending from the tubular housing 1110 to the right. For reference, the cap top 1130 and the ET tube receiving aperture 1104 are called out. Also, the intake tube 1120 depicts the plurality of push connect ring fittings 1128 that encircled the intake tube 1120. The ET oxygen cap 1100 is divided down the middle via section line A-A.

Figure 11C:
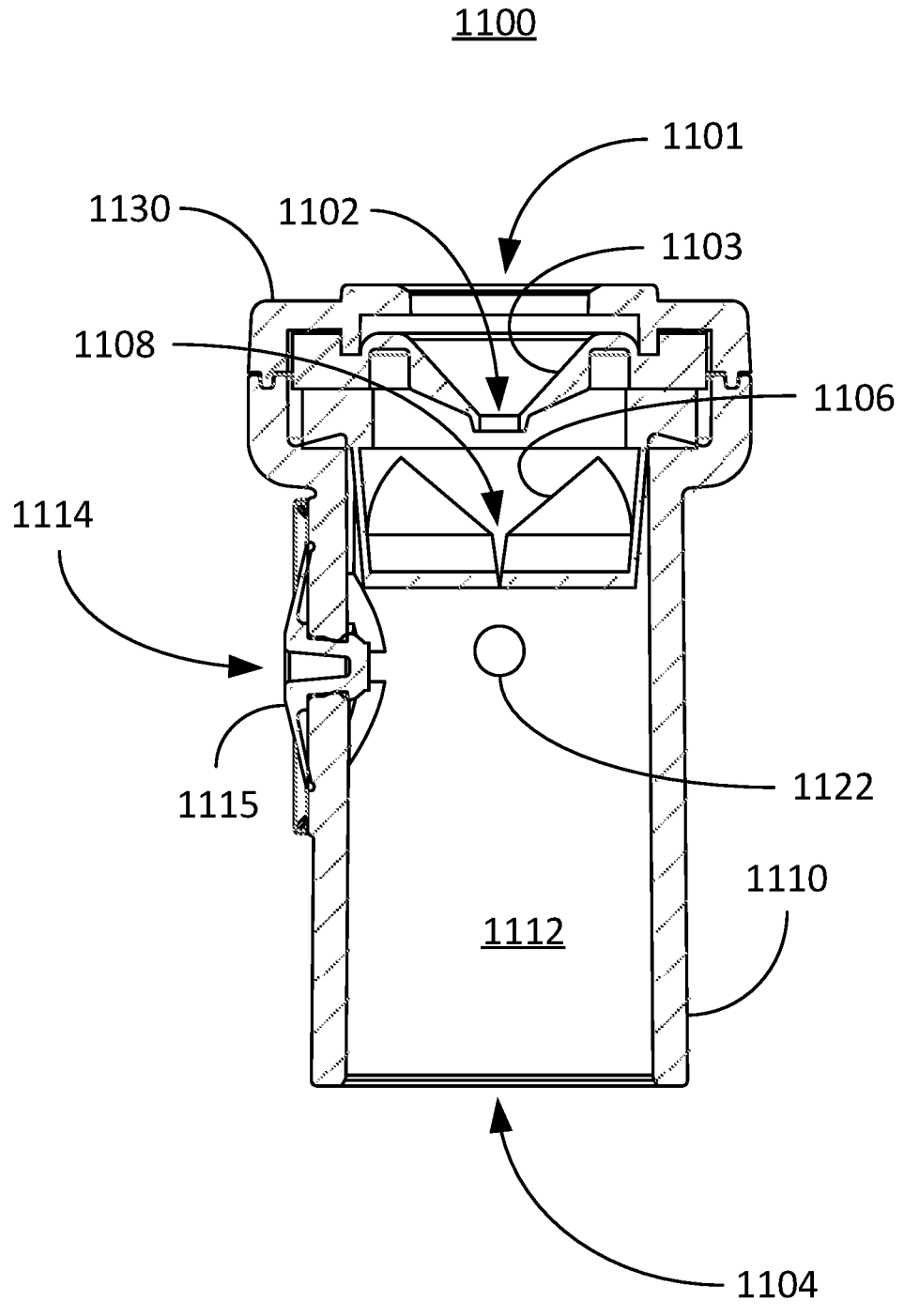

FIG. 11C is a line drawing of a cross-section of the ET oxygen cap 1100 along section line A-A presented in FIG. 11B. From this perspective, the tubular interior housing space 1112 shows four apertures that penetrate through the tubular housing 1110, namely 1) the pressure relief valve aperture 1114, 2) the housing intake port 1122 (which provides communication between the tubular interior housing space 1112 and the distal intake tube port 1124), 3) the ET tube receiving aperture 1104, and 4) the backup seal valve port 1102. With more detail to the instrument port 1101, the major elements include a backup seal valve port 1102, a seal valve port funnel guide 1103, a cross-slit valve 1106, and cross-slit 1108. As mentioned earlier, the instrument port 1101 is configured to receive a stylet, a bronchial scope, or the like (not shown), which could help assist placement of an ET tube 1016 in a patient. In an example of inserting a bronchial scope (not shown) into the instrument port 1101 at the cap top 1130, a bronchial scope is fed through the backup seal valve port 1102, which is sized to the diameter of the bronchial scope. Typical bronchial scope is 2 mm to 5.5 mm in diameter. The ramped surface of the seal valve port funnel guide 1103 funnels the bronchial scope through the backup seal valve port 1102. The backup seal valve port 1102 can be constructed from a flexible silicone or rubber material to help create a seal when the bronchial scope is in the backup seal valve port 1102 thereby preventing oxygen flowing through the housing intake port from escaping through the cap top 1130. The bronchial scope is further fed through the cross-slit 1108 at the center of the cross-slit valve 1106, through the tubular housing interior space and through the distal end of the ET tube 1016. If there is no bronchial scope (or stylet), the cross-slit valve 1106 prevents oxygen entering the ET tube cap 1100 through the housing intake port 1122 from leaking out of, otherwise exiting through, the cap top 1130. As shown in this configuration, the backup seal valve port 1102, the seal valve port funnel guide 1103, and the cross-slit valve 1106 are constructed and/or secured in the instrument port housing 1132.

Figure 11D:
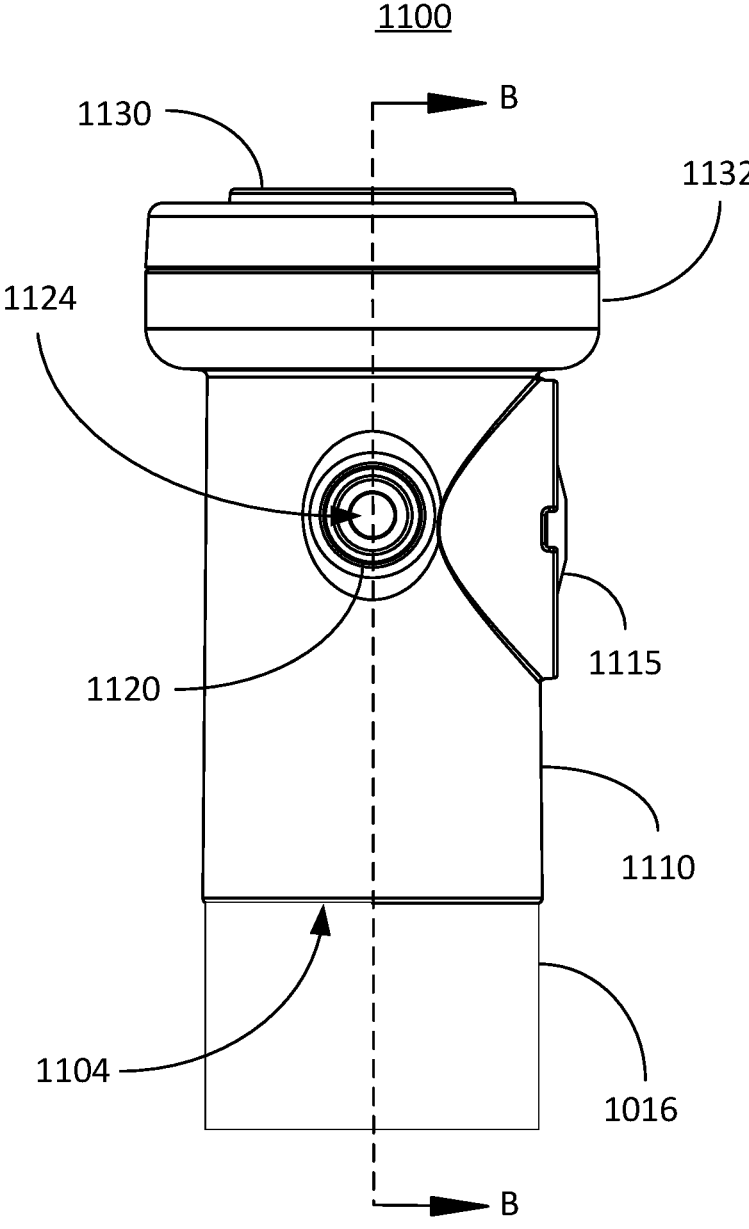

FIG. 11D is a side view line drawing of the ET oxygen cap 1100 with the intake tube 1120 extending from the tubular housing 1110 towards the viewer (out of the page). The tubular passageway of the intake tube 1120 is seen by way of the distal intake tube port 1124. In this configuration, a top portion of an ET tube 1016 is depicted connected to or otherwise extending from the ET tube receiving aperture 1104. A side view of the pressure relief valve 1115 is depicted to the right of the tubular housing 1110. For reference, the cap top 1130 and the instrument port housing 1132 are called out. The ET oxygen cap 1100 is divided down the middle via section line B-B.

Figure 11E:
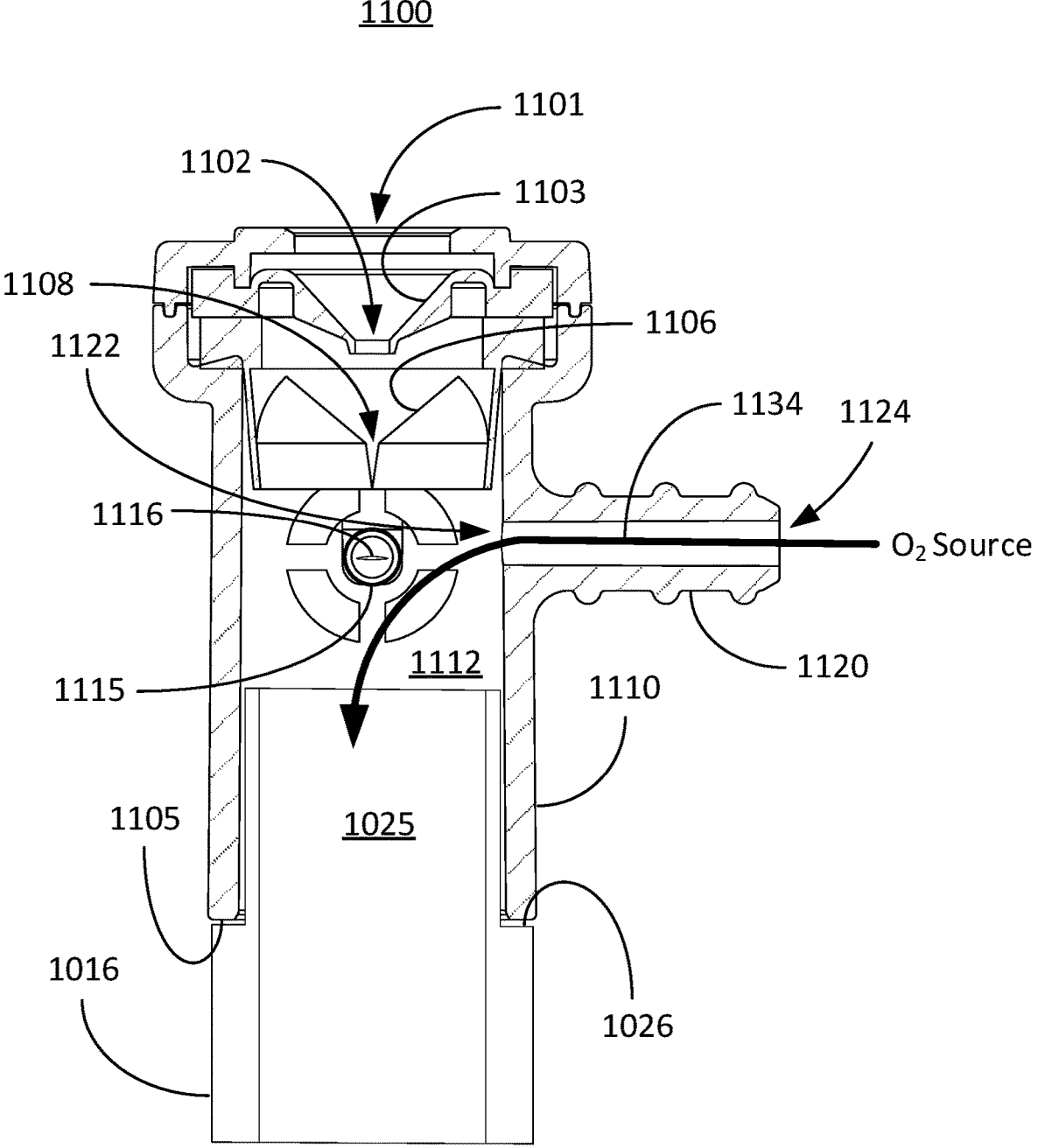

FIG. 11E is a line drawing of a cross-section of the ET oxygen cap 1100 along section line B-B presented in FIG. 11D. From this perspective, the tubular interior housing space 1112 shows the intake tube 1120 extending to the right from the tubular housing 1110 and the pressure relief valve 1115 is facing into the page, which displays a sound producing slit 1116 that produces an audible alarm when cracked open due to an excess pressure buildup in the ET oxygen cap 1100 (from reaching or exceeding a predetermined pressure limit in a patient's lungs). The instrument port 1101, the backup seal valve port 1102, the seal valve port funnel guide 1103, the cross-slit valve 1106, and the cross-slit 1108 are essentially the same as shown in FIG. 11C because the elements are symmetric about the center axis (B-B).

FIGS. 11D and 11E show an upper portion of an ET tube 1016 engaged with the ET tube receiving aperture 1104. As shown in FIG. 11E, this ET tube embodiment 1100 comprises an ET tube ledge 1026 that butts up against the ET tube receiving aperture lip 1105. The ET tube 1016 is retained in the tubular housing 1110 due to being pressure fit inside of the tubular housing 1110 and because of the ET tube ledge 1026 mating with the ET tube receiving aperture lip 1105. No part of the ET tube 1016 obstructs the housing intake port 1122 or the pressure relief valve 1115. Hence, when in operation, oxygen 1134 from an oxygen source is piped through the intake tube 1120 via the distal intake tube port 1122 and made to flow through the tubular housing interior space 1112 and down the ET tube interior 1025 whereby the oxygen 1134 exits the ET tube 1016 to provide oxygen to a patient while being intubated. Oxygen provided to a patient while being intubated reduces the time 'crises' to rapidly deploy or otherwise fully insert an ET tube 1016 in a patient.

Figure 12A:
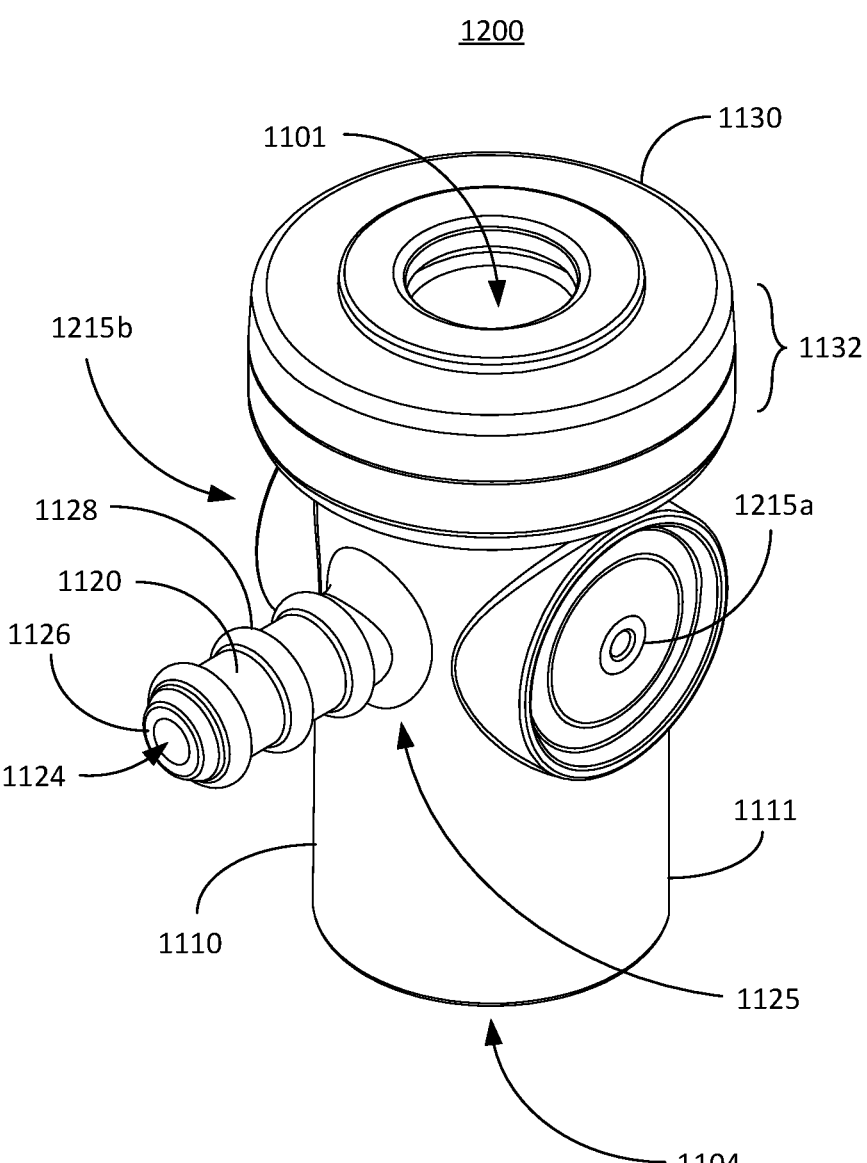
FIGS. 12A-12E are line drawings of yet another optional endotracheal tube cap embodiment consistent with embodiments of the present invention.

FIG. 12A is an isometric view of a dual valve ET, the dual valve ET oxygen cap 1200 generally comprises a tubular housing 1110 that is defined between a cap top 1130 and an ET tube receiving aperture 1104. An intake tube 1120 extends at 90° from the outer side wall 1111 of the tubular housing 1110. The intake tube 1120 is envisioned to connect to an oxygen source via an oxygen tube. The intake tube 1120 is connected to the tubular housing 1110 at a proximal tube end 1125 and extends outwardly terminating at a distal tube end 1126. The intake tube 1120 comprises a plurality of push connect ring fittings 1128 that help retain a flexible tube on the outer surface of the intake tube 1120. Also shown is the distal intake tube port 1124, which provides a path for oxygen to flow into the tubular housing 1110. A pair of pressure relief valves 1215 (which is the designation for the first pressure relief valve 1215a and the second pressure relief valve 1215b) are also located on the outer housing sidewall 1111 at +/−90° from the intake tube 1120. However, the pressure relief valves 1215 can reside in other locations along the outer housing sidewall 1111 (e.g., at +/−120° from the intake tube 112, a first pressure relief valve 1215a at 90° from the intake tube 1120 and a second pressure relief valve 1215b at 180° from the intake tube 1120, just to name a couple of examples), or optionally, one of the pressure relief valves 1215 can be located at the cap top 1130.

The present embodiment includes an instrument port 1101 (located at the cap top 1130) that accommodates a stylet, a bronchial scope, or the like. This instrument port embodiment 1101 is accompanied with an instrument housing backup seal valve 1102 and a cross-slit valve 1106 disposed inside of an instrument port housing 1132. However, other embodiments do not include an instrument port 1101. The dual valve ET oxygen cap 1200 is not intended to be connected to a ventilator, which assists breathing for a distressed person.

Figure 12B:
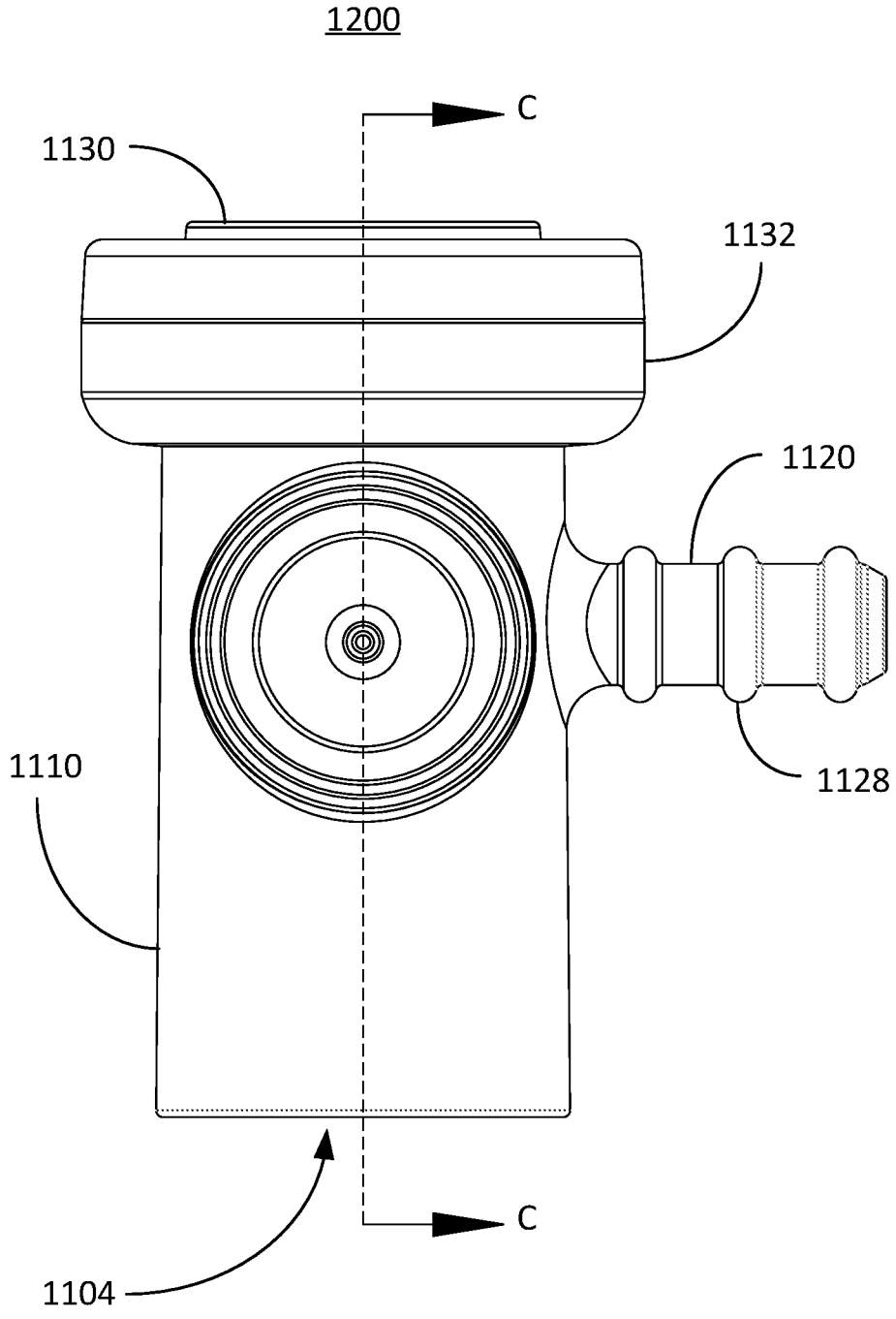

FIG. 12B is a side view line drawing of the dual valve ET oxygen cap 1200. As shown, the intake tube 1120 is extending from the tubular housing 1110 to the right. For reference, the cap top 1130 and the ET tube receiving aperture 1104 are called out. In addition, the intake tube 1120 depicts the plurality of push connect ring fittings 1128 that encircled the intake tube 1120. The dual valve ET oxygen cap 1200 is divided down the middle via section line C-C.

Figure 12C:
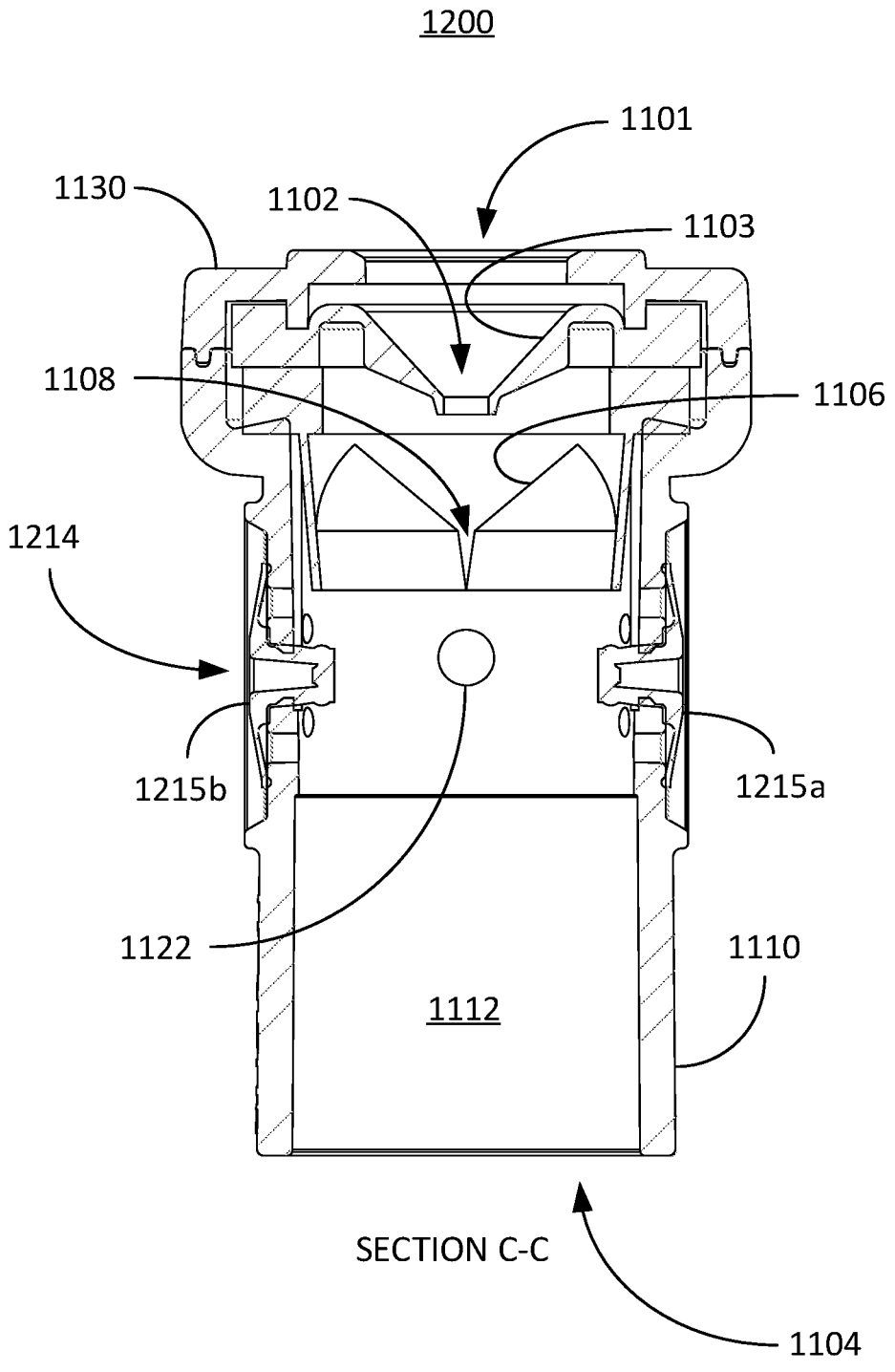

FIG. 12C is a line drawing of a cross-section of the dual valve ET oxygen cap 1200 along section line C-C presented in FIG. 12B. From this perspective, the tubular interior housing space 1112 shows five apertures that penetrate through the tubular housing 1110, namely 1) two pressure relief valve apertures 1214, 2) the housing intake port 1122 (which provides communication between the tubular interior housing space 1112 and the distal intake tube port 1124), 3) the ET tube receiving aperture 1104, and 4) the backup seal valve port 1102. With more detail to the instrument port 1101, the major elements include a backup seal valve port 1102, a seal valve port funnel guide 1103, a cross-slit valve 1106, and cross-slit 1108. As mentioned earlier, the instrument port 1101 is configured to receive a stylet, a bronchial scope, or the like (not shown), which could help assist placement of an ET tube 1016 in a patient. In an example of inserting a bronchial scope (not shown) into the instrument port 1101 at the cap top 1130, a bronchial scope is fed through the backup seal valve port 1102, which is sized to the diameter of the bronchial scope. Typical bronchial scope is 2 mm to 5.5 mm in diameter. The ramped surface of the seal valve port funnel guide 1103 funnels the bronchial scope through the backup seal valve port 1102. The backup seal valve port 1102 can be constructed from a flexible silicone or rubber material to help create a seal when the bronchial scope is in the backup seal valve port 1102 thereby preventing oxygen flowing through the housing intake port from escaping through the cap top 1130. The bronchial scope is further fed through the cross-slit 1108 at the center of the cross-slit valve 1106, through the tubular housing interior space and through the distal end of the ET tube 1016. If there is no bronchial scope (or stylet), the cross-slit valve 1106 prevents oxygen entering the dual valve ET oxygen cap 1200 through the housing intake port 1122 from leaking out of, otherwise exiting through, the cap top 1130. As shown in this configuration, the backup seal valve port 1102, the seal valve port funnel guide 1103, and the cross-slit valve 1106 are constructed and/or secured in the instrument port housing 1132.

Figure 12D:
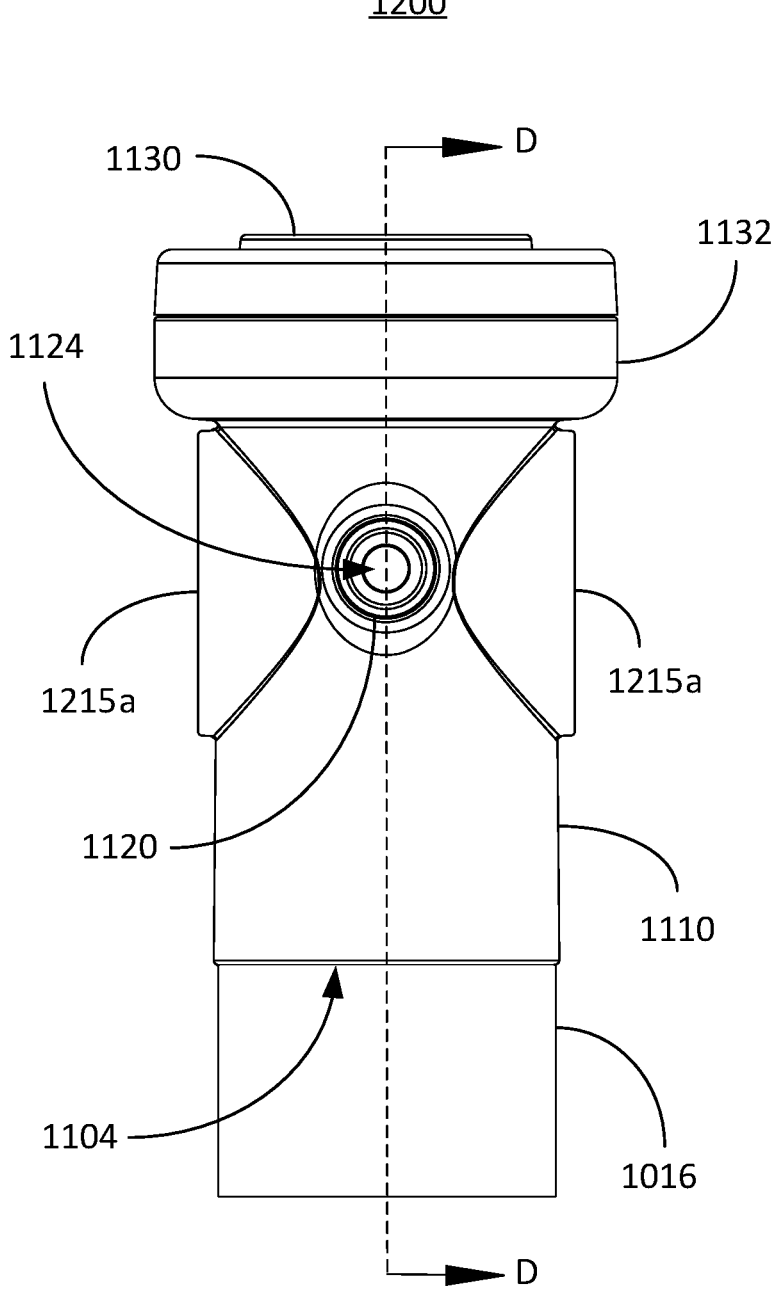

FIG. 12D is a side view line drawing of the dual valve ET oxygen cap 1200 with the intake tube 1120 extending from the tubular housing 1110 towards the viewer (out of the page). The tubular passageway of the intake tube 1120 is seen by way of the distal intake tube port 1124. In this configuration, a top portion of an ET tube 1016 is depicted connected to or otherwise extending from the ET tube receiving aperture 1104. A side view of a first pressure relief valve 1215*a* is depicted to the right side of the tubular housing 1110 and a second pressure relief valve 1215*b* on the left side (opposite side) of the tubular housing 1110. For reference, the cap top 1130 and the instrument port housing 1132 are called out. The dual valve ET oxygen cap 1200 is divided down the middle via section line D-D.

Figure 12E:
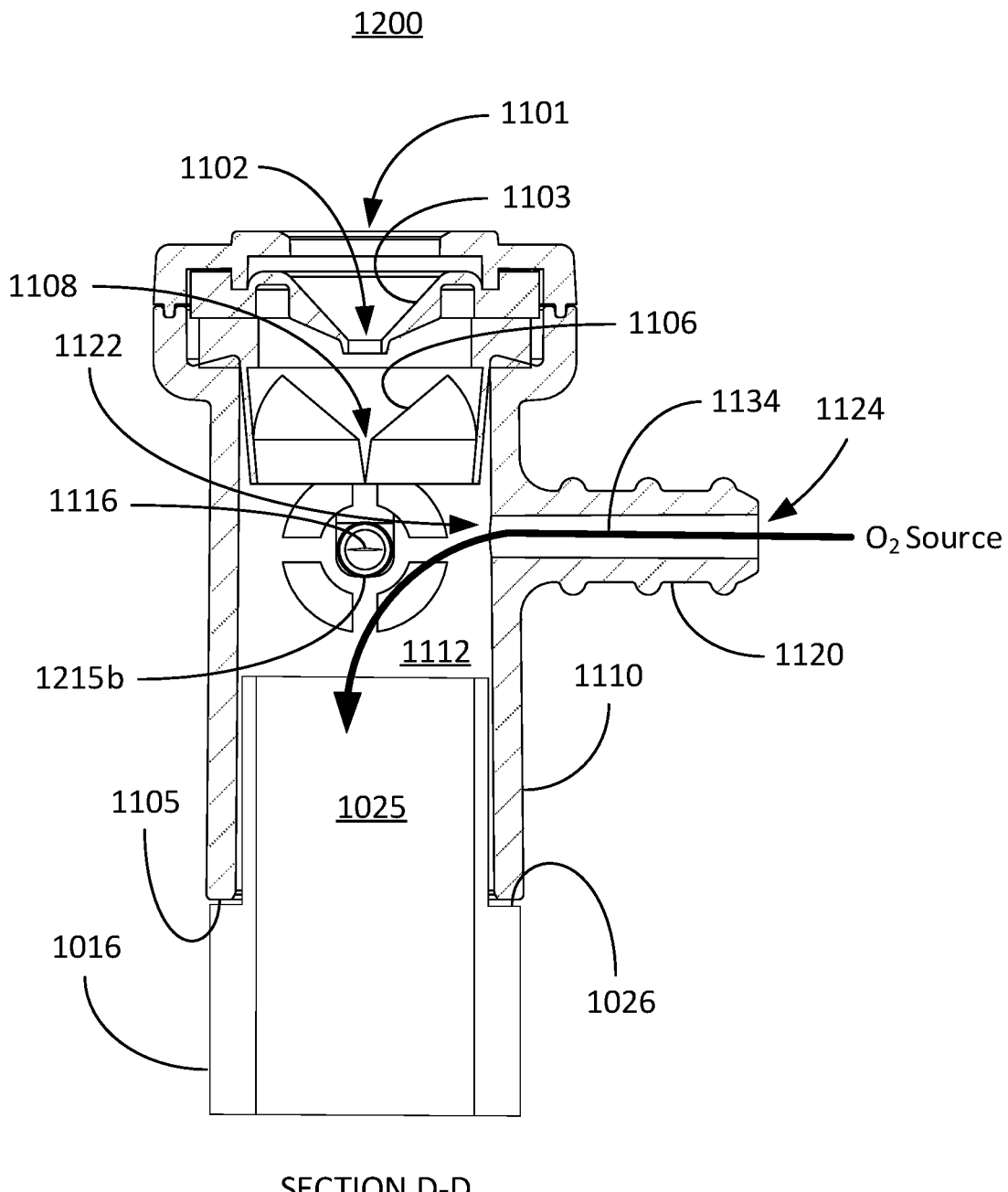

FIG. 12E is a line drawing of a cross-section of the dual valve ET oxygen cap 1200 along section line D-D presented in FIG. 12D. From this perspective, the tubular interior housing space 1112 shows the intake tube 1120 extending to the right from the tubular housing 1110 and the second pressure relief valve 1115*b* is facing into the page, which displays a sound producing slit 1116 that produces an audible alarm when cracked open due to an excess pressure buildup in the dual valve ET oxygen cap 1200 (from reaching or exceeding a predetermined pressure limit in a patient's lungs). The instrument port 1101, the backup seal valve port 1102, the seal valve port funnel guide 1103, the cross-slit valve 1106, and the cross-slit 1108 are essentially the same as shown in FIG. 12C because the elements are symmetric about the center axis (D-D).

FIGS. 12D and 12E show an upper portion of an ET tube 1016 engaged with the ET tube receiving aperture 1104. As shown in FIG. 12E, this dual valve ET oxygen cap embodiment 1200 comprises an ET tube ledge 1026 that butts up against the ET tube receiving aperture lip 1105. The ET tube 1016 is retained in the tubular housing 1110 due to being pressure fit inside of the tubular housing 1110 and because of the ET tube ledge 1026 mating with the ET tube receiving aperture lip 1105. No part of the ET tube 1016 obstructs the housing intake port 1122 or the pressure relief valves 1215. Hence, when in operation, oxygen 1134 from an oxygen source is piped through the intake tube 1120 via the distal intake tube port 1122 and made to flow through the tubular housing interior space 1112 and down the ET tube interior 1025 whereby the oxygen 1134 exits the ET tube 1016 to provide oxygen to a patient while being intubated. Oxygen provided to a patient while being intubated reduces the time 'crises' to rapidly deploy or otherwise fully insert an ET tube 1016 in a patient.

Figure 13A:
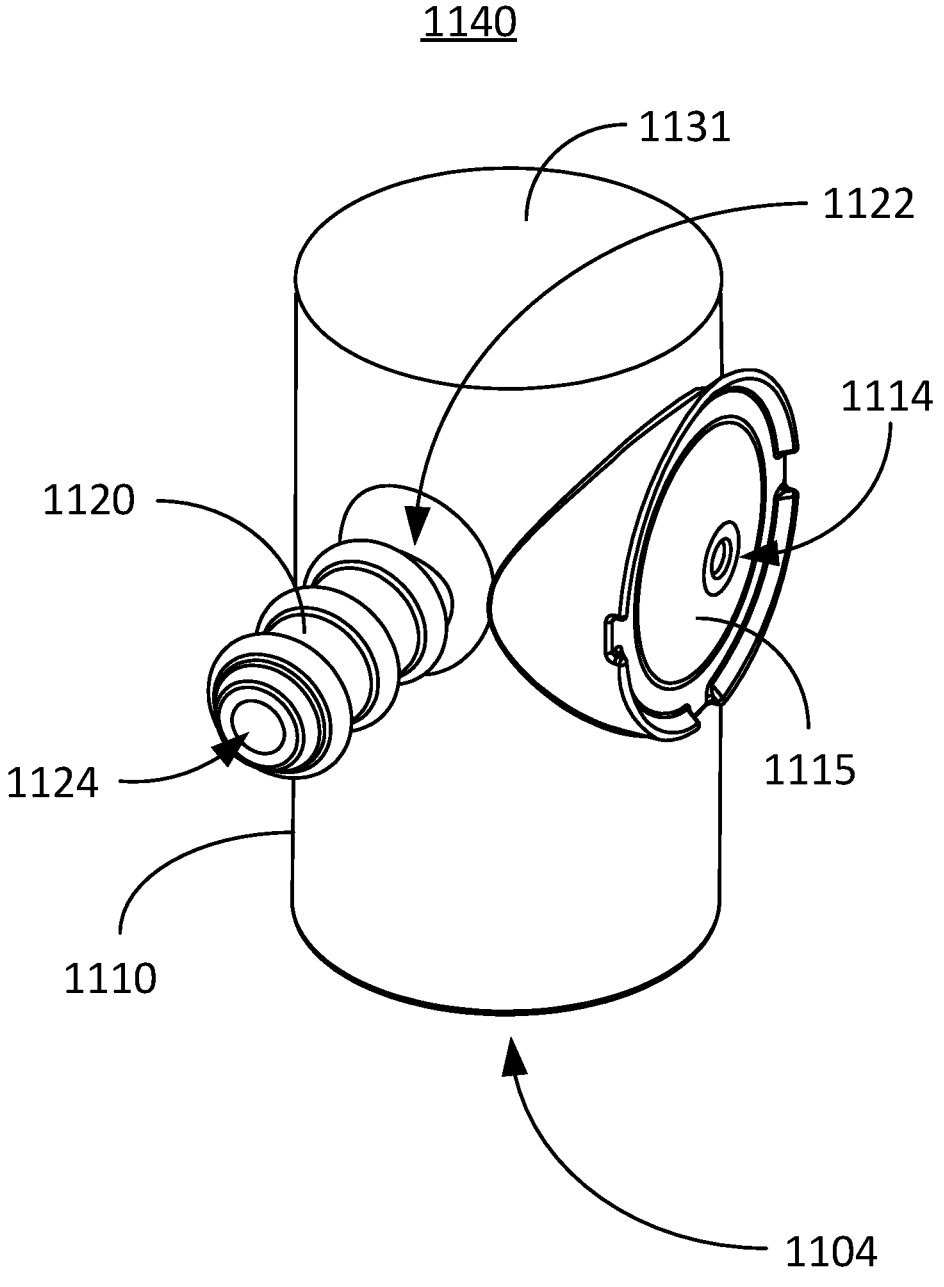
FIGS. 13A and 13B are line drawings of optional endotracheal tube cap embodiments consistent with embodiments of the present invention.
Figure 13B:
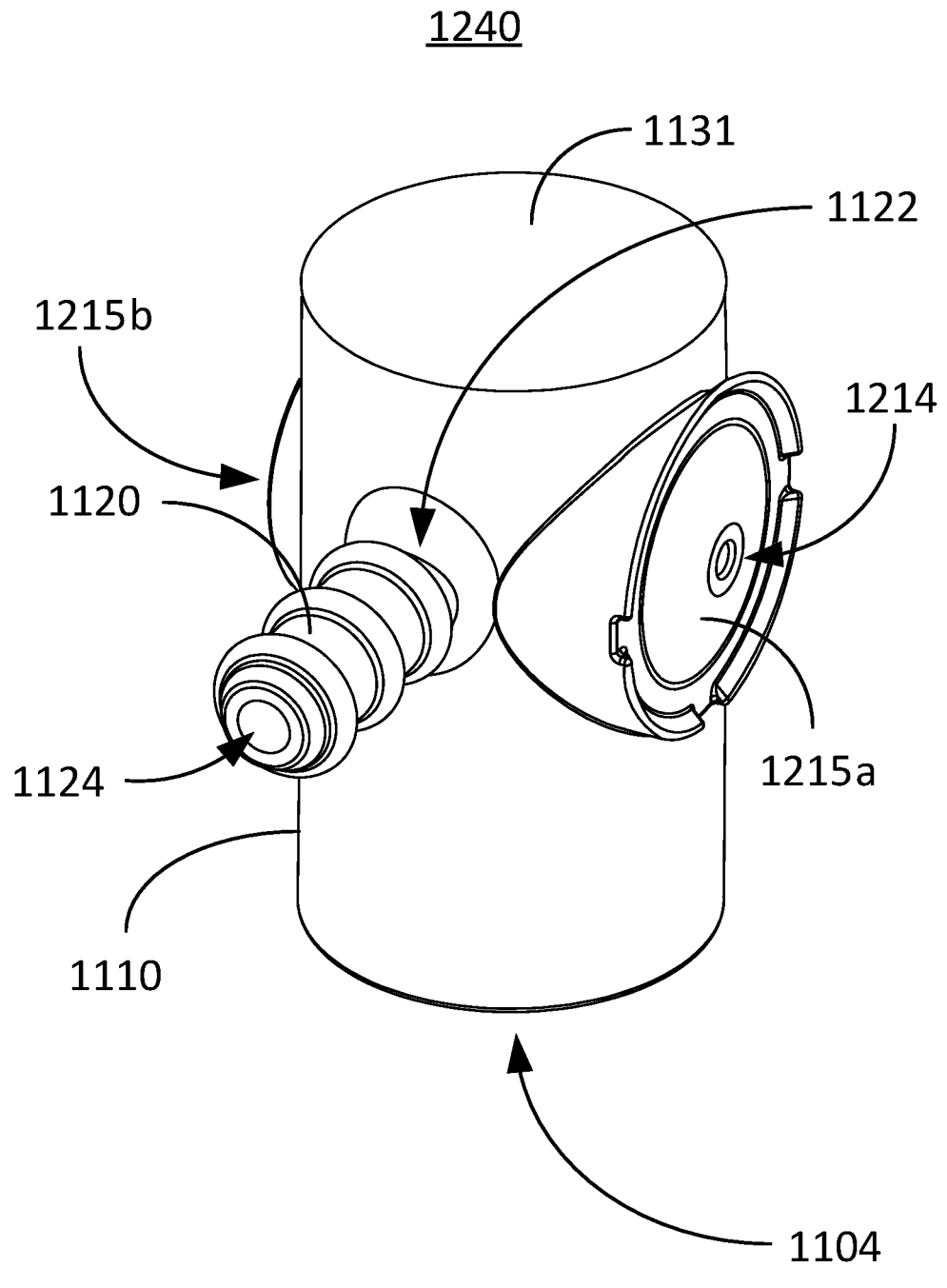

FIGS. 13A and 13B are line drawings of optional ET oxygen cap embodiments consistent with embodiments of the present invention. As shown in FIG. 13A, the single valve ET oxygen cap 1140 is essentially identical to the ET oxygen cap 1100 except there is no instrument port 1101, rather the top 1131 of the ET oxygen cap 1140 is a solid piece of material. In other words, in this embodiment consists of three apertures that are 1) an oxygen intake port 1122 at the tubular housing 1110 (the distal intake tube port 1124 is in communication therewith via the intake tube 1120), 2) a pressure relief valve aperture 1114 (in the center of the pressure relief valve 1115), and 3) the ET tube receiving aperture 1104.

FIG. 13B depicts an optional dual valve ET oxygen cap embodiment 1240 that is essentially identical to the dual valve ET oxygen cap 1200 except there is no instrument port 1101, rather the top 1131 of the dual valve ET oxygen cap 1240 is a solid piece of material. In other words, in this embodiment consists of four apertures that are 1) an oxygen intake port 1122 at the tubular housing 1110 (the distal intake tube port 1124 is in communication therewith via the intake tube 1120), 2) a pressure relief valve apertures 1214 (in the center of each respective pressure relief valves 1215), and 3) the ET tube receiving aperture 1104.

Figure 14:
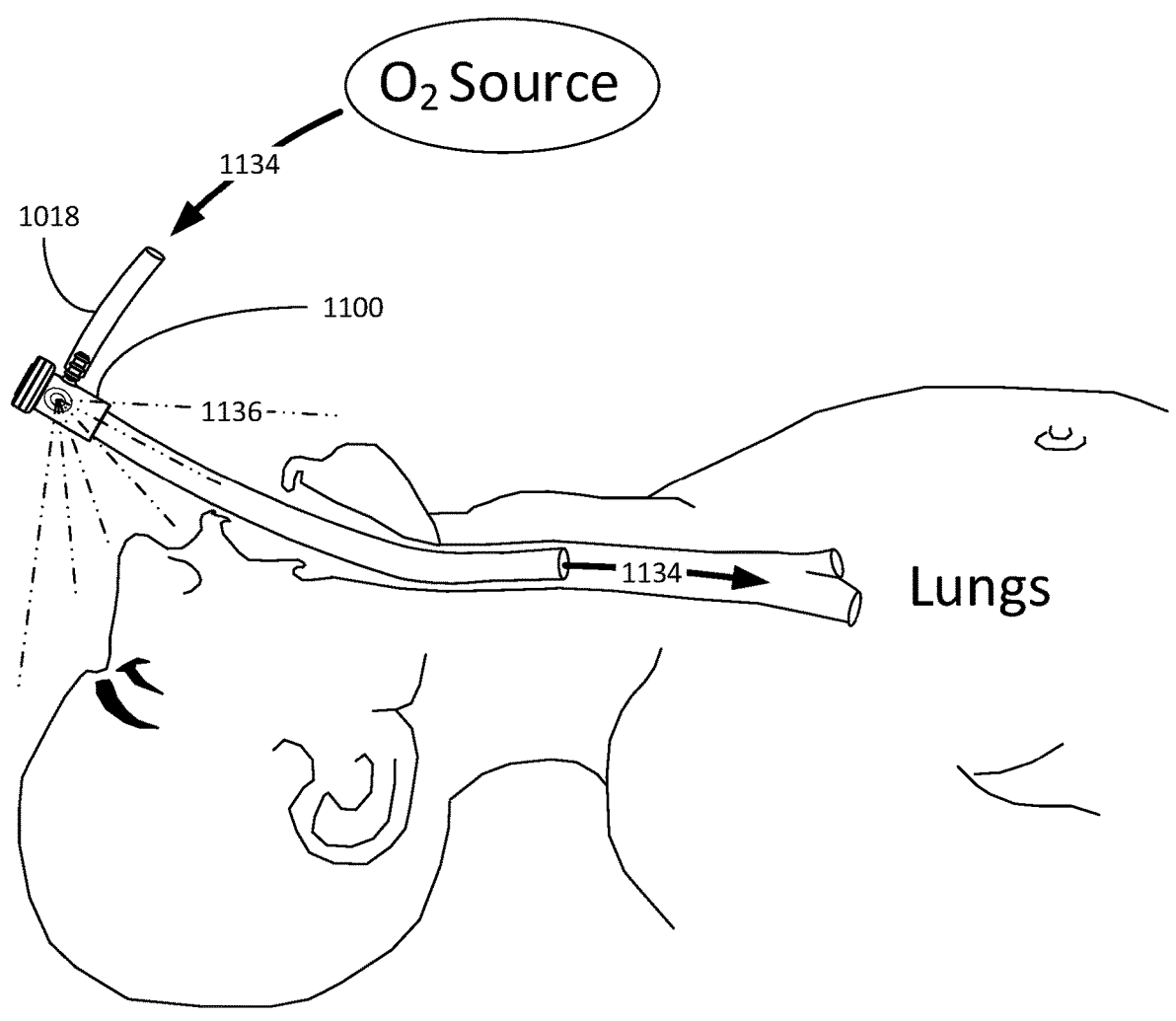
FIG. 14 is a line drawing illustratively depicting a patient getting intubated with ET oxygen cap embodiments consistent with embodiments of the present invention.

FIG. 14 is a line drawing illustratively depicting a patient getting intubated with an ET oxygen cap embodiment consistent with embodiments of the present invention. A patient needing to be intubated is one that is in dire need of oxygen and who is further unable to breathe independently. Today's standard intubation procedure is to quickly (within 30 seconds) deploy an ET tube in the proper location in a patient to commence assisted breathing with a ventilator. In the time it takes to deploy an ET tube, the patient is without oxygen and can suffer harm due to a lack of oxygen (which can occur over an extended period, such as greater than 30 seconds). However, aspects of the present invention envision infiltrating the lungs with a flow of oxygen during intubation to raise blood oxygenation levels in the patient and further provide caretakers with extra time to deploy the ET tube. With this in mind, FIG. 14 pictorially illustrates a method for deploying an ET tube consistent with embodiments of the present invention.

Though equally applicable with the dual valve ET oxygen cap embodiments 1200 and 1240, the following example is directed to using the ET tube 1016 and ET tube cap arrangement 1100. To start, prior to inserting an ET tube in a patient's trachea, an ET tube cap embodiment 1100 (or 1140, 1200, 1240) is connected to A) an oxygen source tube 1018 that is connected to an oxygen source, and B) an ET tube 1016. The ET tube 1016 is cooperatively coupled with the ET tube cap embodiment 1100 via the ET tube receiving aperture 1104. The ET tube cap embodiment 1100 comprises at least a tubular housing 1110 defined between an ET tube receiving aperture 1104 and a cap top 1130, and an intake tube 1120 that extends from the tubular housing 1110 that is connected to the oxygen source tube 1018. As discussed earlier, the intake tube 1120 defines a passageway between a proximal tube end 1125 and a distal tube end 1126 in a manner that the oxygen source is in communication with the ET tube 1016. With oxygen 1134 flowing from the oxygen source through the oxygen source tube 1018 and out the distal end of the ET tube 1016 via the ET tube cap 1100, the next step is to commence intubating the patient. By following this procedure, oxygen 1134 is forced into the patient's lungs. Certain embodiments envision a high percentage of oxygen than the standard 21% in air or even pure oxygen flowing into a patient's lungs via the ET tube 1016.

Certain embodiments of the present invention envision a pressure relief valve 1115 built into the ET tube cap embodiment 1100. If there is high pressure build-up in the patient's lungs that is above a predetermined pressure threshold, such as at or above 20 cm $H_2O$ at 15 liter/min flow rate, the pressure relief valve 1115 will open to relieve the pressure build-up in the lungs by releasing air/oxygen from the pressurized lungs. In another embodiment, the predetermined pressure threshold is at or below 7 cm $H_2O$ at 15 liter/min flow rate whereby the pressure relief valve 1115 will 'crack' or otherwise open at this pressure. At a flow rate that is different, such as 5 liter/min the pressure relief valve 1115 can be made to crack open at 4 cm $H_2O$. This assumes that the oxygen source provides or otherwise flows oxygen at a pressure level higher than a predetermined pressure threshold. In the present embodiment, the pressure relief valve 1115 releases pressure at or above the predetermined threshold. In some embodiments, the pressure relief valve 1115 comprises a slit 1116 or whistle that when pressurized oxygen/air above the predetermined threshold is exiting the pressure relief valve 1115 an audible alarm/whistle 1136 alerts caretakers that there is elevated pressure build-up in the patient's lungs. The alarm 1136 can optionally be created via another sound device other than one or more slits 1116, which are known to those skilled in the art. Certain embodiments envision the oxygen source unable to provide oxygen pressure above the pressure relief valve limit thereby obviating the need for a pressure relief valve.

Accordingly, certain other embodiments envision an ET tube cap embodiment 1000 that is devoid of a pressure relief valve (see FIGS. 10A-10D). Hence, in certain embodiments, the ET tube cap 1000 can have at a minimum two apertures (an oxygen intake port 1008 and an ET tube aperture 1014 at the cap base 1012). The probe port 1004 extending through the cap top 1002 is optional. In this arrangement, pressure can be regulated via the oxygen source or by way of a pressure relief valve in the oxygen source tube 1018 or a pressure relief valve somewhere else along the path prior to the oxygen 1134 reaching the ET tube cap 1000.

Once the patient is fully intubated (i.e., the intubation tube is deployed), the ET tube cap embodiment (e.g., 1100) can be removed and the ET tube 1016 connected to a mechanical ventilator. A mechanical ventilator (as used herein) provides inhalation and exhalation assistance for the patient. That is, a ventilator mechanically 'breathes' for a patient when that patient is not able to breathe independently. Accordingly, in the present embodiment, the ET tube cap embodiments (such as 1000, 1100, 1140) are considered non-ventilator ET tube caps because they are not used in conjunction with a ventilator and are not equipped to assist with a patient's inhalation and exhalation. In other words, the ET tube cap embodiments that are not intended to be coupled with a ventilator (such as 1000, 1100, 1140, 1200 and 1240) and are independent from the ventilator and are not considered connectors that connect ventilators to an ET tube 1016. The non-ventilator ET tube caps (such as 1000, 1100, 1140, 1200 and 1240) are used prior to hooking the patient up to a ventilator via the ET tube 1016.

With the present description in mind, below are some examples of certain embodiments illustratively complementing some of the methods and apparatus embodiments to aid the reader. The elements called out below in view of the various figures are examples provided to assist in understanding the present invention and accordingly should not be considered limiting.

In that light, certain embodiment contemplate an endotracheal tube comprising: a main flexible hollow ET tube 102 that extends in a constant tube diameter 103 from a proximal endotracheal tube end 116, defined by an inlet port 122, to a transition zone (also referred to herein as "joint") 130; a tip 106 that extends from the transition zone 130 to a distal endotracheal tube end 135 defined by an outlet port 124; an uninterrupted pathway 101 extending between the inlet port 122 and the outlet port 124; and at least one tip side aperture 134 in the tip 106 between the transition zone 130 and the outlet port 124, the at least one tip side aperture 134 in communication with the uninterrupted pathway 101, the tip 106 possessing a tip diameter 109 that is at least 20% smaller than the constant tube diameter 103.

The endotracheal tube embodiment further comprising a second pathway 126 defined by a plenum wall 113 inside of the main flexible hollow ET tube 102, the second pathway 126 extending from a plenum inlet port 127 located approximately at the proximal endotracheal tube end 116 at least to a cuff aperture 128 that penetrates through the main flexible hollow ET tube 102, the second pathway 126 not in communication with the uninterrupted pathway 101. This is further imagined wherein the main flexible hollow ET tube

102, the plenum wall 113, the uninterrupted pathway 101 and the second pathway 126 are configured to be formed by polymer extrusion.

The endotracheal tube embodiment further comprising an inflatable cuff 108 attached to the main flexible hollow ET tube 102, the inflatable cuff 108 in communication with the cuff aperture 128, the inflatable cuff 108 configured to be inflated via air passing through the cuff aperture 128. This is further envisioned wherein the proximal endotracheal tube end 116 is configured to mate with a cap arrangement 105, the cap arrangement 105 configured to channel ventilation air to and from the inlet port 122 and to channel cuff air 408 to the inflatable cuff 108.

The endotracheal tube embodiment further contemplating wherein the at least one tip side aperture 134 and the outlet port 124 collectively define a total port area 148 that is equal to or greater than an uninterrupted pathway area 142 defined by uninterrupted pathway radial plane 146 in the uninterrupted pathway 101.

The endotracheal tube embodiment further considering wherein the tip 106 tapers from the constant tube diameter 103 at the transition zone 130 to the distal endotracheal tube end 135, the distal endotracheal tube end 135 defining the tip diameter 109. This is further imagined wherein the tip 106 is a contiguous part of the flexible hollow ET tube 102 that is adapted to be formed by heating and pulling. Optionally, this is further imagined wherein the tip 106 is attached to the flexible hollow ET tube 102 at the transition zone 130.

The endotracheal tube embodiment is further envisioned wherein the cap arrangement 105 comprises a cap 300 that fits over a portion of a cap body 302 in a rotating relationship. This can additionally be wherein the cap 300 possesses a ventilation port 320 and an oxygen port 322 that are each defined by tubes that extend radially from the cap 300. This can additionally be wherein the cap body 302 possesses a ventilation aperture 306 and an inflatable cuff intake aperture 307, that each penetrate through the cap body 302. When the cap 300 is cooperating with the cap body 302 in a first rotational arrangement, the inflatable cuff intake aperture 307 is in alignment with the oxygen port 322. The ventilation aperture 306 is in alignment with the ventilation port, when the cap 300 is cooperating with the cap body 302 in a second rotational arrangement, and the inflatable cuff intake aperture 307 and the oxygen port 322 are in alignment, but the ventilation aperture 306 is not in alignment with the ventilation port 320. Additionally, this can further be wherein when the cap 300 cooperates with the cap body 302 in a third rotational arrangement, the oxygen port 322 is in alignment with the ventilation aperture 306, but the inflatable cuff intake aperture 307 is not in alignment with the oxygen port 322 and the ventilation aperture 306 is not in alignment with the ventilation port 320. An additional embodiment is wherein the oxygen port 322 is configured to deliver at least 95% pure oxygen and wherein the ventilation port 320 is adapted to deliver a predetermined oxygen and nitrogen ratio.

The endotracheal tube embodiment further contemplating wherein the cap 300 is an essentially rigid and the cap body 302 is pliable.

The endotracheal tube embodiment further envisaging wherein the cap body 300 tube further possesses a bite surface 304 that covers a bite void 366, the bite void 366 adapted to collapse when a patient bites down on the cap body 302 when positioned at teeth belonging to the patient when the ET tube 102 is deployed in the patient.

The endotracheal tube embodiment further considering wherein the cap arrangement 105 further possesses a cap plug 312 that removably covers a cap assembly channel 101 aligned with the uninterrupted pathway 101. Removably covers means the cap plug 312 is able to be removed from the probe port 310 that it covers.

The endotracheal tube embodiment further imagining wherein the cap 300 slidingly locks onto the cap body 302 by way of a clip to groove relationship wherein the cap 300 possesses a clip 332 and the cap body 302 possesses a groove 360.

Other embodiments imagine an endotracheal tube comprising: a tip 106 that extends from a flexible hollow ET tube 102, the flexible hollow ET tube 102 having a constant tube outer diameter 103, the tip 106 tapering from the constant tube outer diameter 103 to a tip outer diameter that is less than 10% smaller than the constant tube outer diameter 103; an uninterrupted pathway 101 extending between an inlet port 122 located at a proximal end 116 of the a flexible hollow ET tube 102 and an outlet port 124 located at a distal end 135 of the tip 106; and at least two tip side apertures 134 defined by apertures in a side of the tip 106 between the constant outer tube diameter 103 and the outlet port 124, the tip side apertures 134 in communication with the uninterrupted pathway 101.

The endotracheal tube embodiment further comprising a second pathway 126 defined by a plenum wall 113 and an inside lengthwise portion of the flexible hollow ET tube 102, the second pathway essentially extending from the proximal end 116 to the tip 106; at least to a cuff aperture 128 passing through the flexible hollow ET tube 102, the second pathway 126 not in communication with the uninterrupted pathway 101. This is further contemplated wherein the second pathway is defined by essentially an inside lengthwise portion of the ET tube 102 and the plenum wall 113. This is further imagined wherein the portion of the ET tube 102 makes up at least 30% of inner walls defining the second pathway 126. This can further comprising an inflatable cuff 108 attached to the flexible hollow ET tube 102, the inflatable cuff 108 in communication with the cuff aperture 128, the inflatable cuff 108 configured to be inflated via the cuff aperture 128.

The endotracheal tube embodiment further comprising an uninterrupted pathway cross-sectional area 142 defined by a plane passing orthogonally through the uninterrupted pathway, the outlet port 124 and the tip side apertures 134 defining a collective port area 148 through which air is configured to pass, the collective port area 148 equal to or greater than the uninterrupted pathway cross-sectional area 142.

Yet other embodiments contemplate an endotracheal tube apparatus 100 comprising: a flexible hollow ET tube 102 that extends between a first tube end 116 and a second tube end 118, the ET tube 102 is essentially defined by a constant tube diameter 103, the first end 116 possessing a tube inlet port 122; and a tip 106 joined 130 with the ET tube 102 at the second tube end 118, the tip 106 tapered 107 from a first tip diameter 103 where the tip 106 is joined 130 with the second end 118 to a second tip diameter 109 at essentially a tip distal end 135, the second tip diameter 109 smaller than the first tip diameter 103, the tip distal end 135 terminating in a tip distal outlet port 124, the tip 106 including at least one tip side port 134 located between where the tip 106 is joined 130 with the second end 118 and the distal end 135, the tube inlet port 122 is in communication with the tip distal outlet port 124 and the at least one tip side port 134 via a contiguous passageway 101.

The endotracheal tube apparatus 100 embodiment further considering wherein the second tip diameter 109 is at least 20% smaller than the tube diameter 103.

The endotracheal tube apparatus 100 embodiment further imagining wherein the tip 106 is a unitary part of the ET tube 102.

The endotracheal tube apparatus 100 embodiment further comprising a rotatable cap arrangement 305 joined to an inlet region 110 of the ET tube 102, the inlet region 110 is defined from the first tube end 116 to where the endotracheal tube 102 is adapted to interface with a human soft palate, the rotatable cap arrangement 105 possesses an oxygen port 322 and a ventilation port 320, when the rotatable cap arrangement 305 is in a first position the oxygen port 322 is in communication with the contiguous pathway 101 and when the rotatable cap arrangement 305 is in a second position the ventilation port 320 is in communication with the contiguous path 101, the ventilation port 320 and the oxygen port 322 cannot be in communication with the contiguous pathway 101 at the same time.

The endotracheal tube apparatus 100 embodiment further contemplating wherein the oxygen port 322 is an oxygen tube that extends radially from the rotatable cap arrangement 105, the oxygen port 322 aligning with an inlet aperture 306 when in the first position, the inlet aperture 306 forming an unobstructed path through the ET tube 102 at the inlet region 110. This is further envisioned wherein the ventilation port 320 is a ventilation tube that extends in the radial direction, the ventilation tube 320 aligning with the inlet aperture 306 when the second position. Optionally, this can be wherein the rotatable cap arrangement 105 further includes a removable cap plug 312 that covers a probe port 310 that is axially aligned with the tube inlet port 122. This can further be wherein the probe port 310 is adapted to receive a rigid arced guide that is configured to guide the tip 106 into a human trachea. Optionally, this can be wherein the probe port 310 is adapted to receive an endoscope that is configured to provide visual images as seen through the tip 106.

The endotracheal tube apparatus 100 embodiment further comprising: an inflatable cuff 108 attached to an exterior wall 111 of the ET tube 102 in a distal region 112 of the ET tube 102; and a second pathway 126 inside of the ET tube 102 exiting through a cuff port 128 in the distal region 112 of the ET tube 102, the inflatable cuff 108 in communication with the second pathway 126 via the cuff port 128. This can further be wherein the second pathway 126 is an extruded plenum in the ET tube 102. Optionally, this can be wherein the inflatable cuff 108 is attached approximately to where the tip 106 is joined with the second end 118 at joint 130. Or yet another option is wherein when the rotatable cap arrangement 105 is in a third position, the second pathway 126 inside the ET tube 102 is in communication with the oxygen port 122, the second pathway 126 cannot be in communication with the oxygen port 122 when the rotatable cap arrangement 105 is in the first position.

Still, yet another embodiment of the present invention contemplates an endotracheal tube cap arrangement 105 comprising: a cylindrically shaped inlet body 302 having a hollow core 333; a cuff inflation aperture 307 passing through a side wall 321 of the inlet body 302 into a cuff inflation pathway 126; a ventilation aperture 306 passing through the side wall 321 to the hollow core 333; a cap 300 rotatingly engaged with the inlet body 302, the cap 300 covering an upper portion 339 of the inlet body 302 that includes the cuff inflation aperture 307 and the ventilation aperture 306; an oxygen inlet tube 322 defining an oxygen inlet passageway 336 extending from the cap 300 and a ventilation tube 320 defining a ventilation tube passageway 338 extending from the cap 300, when the cap 300 is in a first rotational position on the inlet body 302 the oxygen inlet passageway 336 is aligned with the cuff inflation aperture 307, when the cap 300 is in a second rotational position on the inlet body 302 the ventilation tube passageway 338 is aligned with the ventilation aperture 306, the cap arrangement 105 configured to matingly connect with a proximal end of an endotracheal tube.

The cap arrangement 105 embodiment further comprising a probe port 310 in the top of the cap 300 that is axially aligned with the hollow core and leads into the hollow core, and a removable cap plug 312 configured to removably cover and seal the probe port 310 from an external environment.

The cap arrangement 105 embodiment further considering wherein when the cap 300 is in a third rotational position on the inlet body 302, the oxygen inlet passageway 336 is aligned with the ventilation aperture 306, but not the cuff inflation aperture 307. This can be wherein when the cap 300 is in the third rotational position on the inlet body 302, the ventilation tube passageway 338 is not aligned with the ventilation aperture 306, and the oxygen inlet passageway 336 is not aligned with the cuff inflation aperture 307.

The cap arrangement 105 embodiment further imagining wherein when the cap 300 is in the second rotational position on the inlet body 302, the ventilation tube passageway 338 is aligned with the ventilation aperture 306, but the oxygen inlet passageway 336 is not aligned with the cuff inflation aperture 307.

The cap arrangement 105 embodiment further considering wherein when the cap 300 is in the second rotational position on the inlet body 302, the ventilation tube passageway 338 is aligned with the ventilation aperture 306, and the oxygen inlet passageway 336 is aligned with the cuff inflation aperture 307.

The cap arrangement 105 embodiment further contemplating wherein the cap 300 further possesses a lip 332 that engages a circumferential groove 360 in the cylindrically shaped inlet body 302, when the lip 332 is engaged with the groove 360 and the cap 300 is retained over the upper portion 339 of the inlet body 302.

The cap arrangement 105 embodiment further conceiving wherein the cylindrically shaped inlet body 302 possesses a bite void 366 located in a lower portion 341 of the inlet body 302, and the lower portion 341 is not covered by the cap 300. This can be wherein the cylindrically shaped inlet body 302 is a pliable polymeric material and the cap 300 is rigid compared to the pliable polymeric material.

The cap arrangement 105 embodiment further imagining wherein the cylindrically shaped inlet body 302 possesses a top surface 350 with indicia 344, viewable through a slot in the cap 300.

While still another embodiment of the present invention considers a method comprising: providing an endotracheal tube cap arrangement 105 that has a cylindrically shaped inlet body 302 with a hollow core 333, a cuff inflation aperture 307 passing through a side wall 321 of the inlet body 302 into a cuff inflation pathway 126, a ventilation aperture 306 passing through the side wall 321 to the hollow core 333, a cap 300 rotatingly engaged with the inlet body 302, the cap 300 covering an upper portion 339 of the inlet body 302 that includes the cuff inflation aperture 307 and the ventilation aperture 306, an oxygen inlet tube 322 extending from the cap 300 and defining an oxygen inlet passageway 336 and a ventilation tube 320 also extending from the cap 300 and defining a ventilation tube passageway 338, and an ET tube 102 matingly connected to a bottom side 365 of the inlet body 302; connecting a first air hose 904 to the oxygen inlet tube 322 and a second air hose 902 to the ventilation tube 320; rotating the cap 300 in a first position where the oxygen inlet tube 322 is in line with the ventilation aperture 306, but not in line with the cuff inflation aperture 307, and the ventilation tube 320 is not in line with any of the apertures 306 and 307; and deploying the ET tube 102 into a trachea while first air supplied by the first air hose 904 is moving through the oxygen inlet passageway 336, through the ventilation aperture 306, through the hollow core 333 and through an exit port 124 of the ET tube 102.

The method embodiment further comprising: after the deploying step when the ET tube 102 is fully deployed in the trachea, rotating the cap 300 to a second position where the oxygen inlet tube 322 is no longer in line with the ventilation aperture 306 but is in line with the cuff inflation aperture 307, with the oxygen inlet tube 322 in line with the cuff inflation aperture 307 inflating an inflatable cuff 108 attached to the ET tube 102 via the first air 702 moving through the oxygen inlet passageway 336, through the cuff inflation aperture 307, through a dedicated pathway for the inflatable cuff 108 and into the inflatable cuff 108. This embodiment can further comprise: after rotating the cap 300 to the second position, rotating the cap 300 to a third position where the a ventilation tube 320 is in line with the ventilation aperture 306; moving ventilation air through the second air hose 902, the tube passageway 338, the ventilation aperture 306, the hollow core 333, the ET tube 102 and the exit port 124 of the ET tube 102. This can be wherein the oxygen inlet tube 322 remains in line with the cuff inflation aperture 307. This can additionally be wherein the oxygen inlet tube 322 and the ventilation tube 320 extend radially from the cap 300.

The method embodiment further envisioning wherein the cap 300 is rotating attached to the inlet body 302 by way of a lip 360 on the cap 300 that is engaged with a groove 360 in the inlet body 302.

The method embodiment further considering wherein the first air source has a concentration of oxygen above 90%.

Another embodiment of the present invention considers an optional method comprising: providing an endotracheal tube cap arrangement 105 that includes a rotatable cap 300 that possesses an enriched oxygen source and a ventilation air source, and an ET tube 102 connected to the endotracheal tube cap arrangement 105; with the endotracheal tube cap arrangement 105 in a first position moving enriched oxygen 408 from the enriched oxygen source through an exit port 124 of the ET tube 102; intubating a trachea while the enriched oxygen 408 is moving through the exit port 124, and while ventilation air is blocked from the ventilation air source.

The method embodiment further comprising, after the intubating step, rotating the cap 300 to a second position, while in the second position the enriched oxygen 408 is moving through a dedicated pathway into an inflatable cuff 108 connected to the ET tube 102 and an inflatable cuff 108 connected to the ET tube 102. This can even further comprise, after the rotation of the cap 300 to the second position, rotating the cap 300 to a third position, while in the third position moving the ventilation air through the exit port 124 and into the trachea.

Another apparatus embodiment imagines an endotracheal tube cap 1000 comprising: a hollow core 1015 inside of a cylindrically shaped cap housing 1010, the housing 1010 defining a cap top 1002 and a cap base 1012; an oxygen intake tube 1006 extending from the cap housing 1010 and terminating in an oxygen intake port 1008, the oxygen intake tube 1006 configured to fixedly cooperate with an oxygen source tube 1018; the hollow core 1015 extending through an endotracheal tube aperture 1014 at the cap base 1012, the endotracheal tube aperture 1014 configured to receive an endotracheal tube 1016, the endotracheal tube cap 1000 configured to essentially form an airtight seal around the endotracheal tube 1016 when a cooperating relationship with the endotracheal tube 1016 via the endotracheal tube aperture 1014; and an uninterrupted oxygen pathway 1022 extending from the oxygen intake port 1008, through the oxygen intake tube 1006, through the hollow core 1015 and to the endotracheal tube aperture 1014.

The endotracheal tube cap 1000 embodiment further envisioning wherein the oxygen intake tube 1006 extends radially from the cylindrically shaped cap housing 1010.

The endotracheal tube cap 1000 embodiment further contemplating wherein enriched oxygen is configured to flow through the oxygen source tube 1018, through the uninterrupted oxygen pathway 1022 and through the endotracheal tube 1016.

The endotracheal tube cap 1000 embodiment further conceiving wherein the cap top 1002 is sealed off from an exterior environment. This can additionally be wherein the cap top 1002 is sealed off from the exterior environment by way of a removable cap plug 312, sealing a probe port 1004.

The endotracheal tube cap 1000 embodiment further envisaging wherein the oxygen intake tube 1006 possesses a chamfered edge 1009 at the oxygen intake port 1008, configured to rapidly receive the oxygen source tube 1018.

The endotracheal tube cap 1000 embodiment further imagining wherein the cylindrically shaped cap housing 1010 possesses a chamfered edge 1011 at the endotracheal tube aperture 1014 configured to rapidly receive the endotracheal tube 1016.

In another embodiment, an intubation method is envisioned comprising: providing an endotracheal tube cap 1000 that is defined by a hollow core 1015 inside of a cylindrically shaped cap housing 1010, the hollow core 1015 in communication with an endotracheal tube aperture 1014 located at a base side 1012 of the housing 1010, an oxygen intake tube 1006 extending from the housing 1010 and terminating in an oxygen intake port 1008; manually pressing an oxygen source tube 1018 into the oxygen intake port 1008 and manually pressing a proximal end 1023 of an endotracheal tube 1016 into the endotracheal tube aperture 1014; after the pressing steps, flowing oxygen through the oxygen source tube 1018, then through the oxygen intake tube 1006 via the oxygen intake port 1008, then through the hollow core 1015, then through the endotracheal tube aperture 1014, and out of a distal aperture (not shown) in the endotracheal tube 1016; and after the flowing step, inserting the endotracheal tube 1016 into a trachea.

The intubation method embodiment further contemplating wherein the oxygen intake tube 1006 possesses in intake chamfer 1009 that increases the oxygen intake port 1008 to at least 5% larger than the oxygen source tube 1018. This can additionally be wherein the oxygen source tube 1018 fits snugly inside of the oxygen intake tube 1006 beyond where the intake chamfer 1009 ends.

The intubation method embodiment additionally conceiving wherein housing 1010 possesses a chamfered edge 1011 at the endotracheal tube aperture 1014 that increases the endotracheal tube aperture 1014 at least 5% larger than the outer diameter of the endotracheal tube 1016. This can further be wherein the endotracheal tube 1016 snugly fits inside of the hollow core 1015 beyond where the chamfered edge 1011 ends.

The intubation method embodiment further comprising, after the insertion step and when the endotracheal tube 1016 is fully inserted into the trachea, manually removing the endotracheal tube cap 1000 from the endotracheal tube 1016 and attaching a ventilator to the endotracheal tube 1016 to where the endotracheal tube cap 1000 was pressed.

The intubation method embodiment further comprising removing a cap plug 312 from a probe port 1004 in a top portion of the housing 1010, the cap plug 312 configured to seal the probe port 1004.

The intubation method embodiment additionally considering wherein the oxygen intake tube 1006 extends radially from the cylindrically shaped cap a housing 1010.

A separate embodiment of the present invention if for an intubation method comprising: prior to inserting an endotracheal tube 1016 into a trachea, attaching an oxygen source tube 1018 to an oxygen intake tube 1006 and attaching the endotracheal tube 1016 to an endotracheal tube aperture 1014, an endotracheal tube cap 1000 comprises the oxygen intake tube 1006 and the endotracheal tube aperture 1014; and flowing enriched oxygen through the endotracheal tube cap 1000 from the oxygen source tube 1018 and out of an exit port (not shown) of the endotracheal tube 1016 while inserting the endotracheal tube 1016 into the trachea.

The intubation method embodiment further envisioning wherein flowing the enriched oxygen through the endotracheal tube 1000 is by way of flowing the enriched oxygen into the oxygen intake tube 1006 and out of the endotracheal tube aperture 1014 and into the endotracheal tube 1016.

The intubation method embodiment additionally considering wherein the endotracheal tube cap 1000 is defined by a hollow core 1015 inside a cylindrically shaped cap housing 1010, the hollow core 1015 in communication with a) the endotracheal tube aperture 1014 located at a base side 1012 of the housing 1010 and b) the oxygen intake tube 1006 which extends radially from the housing 1010 and terminating in an oxygen intake port 1008.

The intubation method embodiment further comprising manually pressing the oxygen source tube 1018 into the oxygen intake port 1008, the oxygen intake port 1008 defined by an oxygen intake port chamfer 1009 that enlarges the oxygen intake port 1008 at least 5% larger in diameter than the oxygen source tube inner diameter 1019 of the oxygen source tube 1018; and manually pressing a proximal end of an endotracheal tube 1016 into the endotracheal tube aperture 1014 that is at least 5% larger in diameter than an inner diameter hollow core diameter 1017 of the hollow core 1015.

The intubation method embodiment further comprising inserting the endotracheal tube 1016 into a trachea while oxygen enriched air is flowing through the exit port. This can further comprise after the insertion step, removing the endotracheal tube cap 1000 from the endotracheal tube 1016 and replacing the endotracheal tube cap 1000 with a ventilation tube 902.

Still yet another embodiment of the present invention contemplates an endotracheal (ET) tube cap 1100 comprising: a tubular housing 1110 defined between an ET tube receiving aperture 1104 and a cap top 1130; an intake tube 1120 that extends from the tubular housing 1110, the intake tube 1120 comprising an unobstructed passageway between a proximal tube end 1125 and a distal tube end 1126, the proximal tube end 1125 defining a housing intake port 1122 that extends through the tubular housing 1110 and the distal tube end 1126 defining a distal tube port 1124; at least one pressure relief valve 1115 or 1215a/1215b that opens when pressure inside of the ET tube cap 1100 exceeds a predetermined pressure threshold, when the ET tube cap 1100 is connected to an ET tube 1016 at the ET tube receiving aperture 1104 and the intake tube 1120 is connected to an external gas source, the external gas source is in communication with the ET tube 1016 via the intake tube 1120, the ET tube cap 1100 is independent of connection with a ventilator. Independent of connection with a ventilator is defined herein as the ET tube cap 1100 (or similar embodiment) never being physically connected to a ventilator. Simply put, an ET cap 1100 that is independent of connection with a ventilator means that it is not used with a ventilator and to do so would require unwanted modification of the ET cap 1100 thereby changing the principle of operation of the ET cap 1100.

The ET tube cap embodiment 1100 further imagining the pressure relief valve 1115 comprising a whistle that produces sound when the pressure relief valve 1115 is opened.

The ET tube cap embodiment 1100 can further comprise an instrument port 1101 that leads to a cross-slit valve 1106, the instrument port 1101 is located at the cap top 1130. The ET tube cap embodiment can further be wherein the cross-slit valve 1106 blocks all airflow through the cap top 1130 when closed.

The ET tube cap embodiment 1100 further envisioning the cap top 1130 being a cover that permanently blocks an interior portion of the tubular housing 1110.

The ET tube cap embodiment 1100 further pondering the intake tube 1120 being connected to the external gas source via a gas line 1018. Optionally, the external gas source is oxygen 1134, such as pure oxygen or a higher than 21% oxygen concentration as in normal air.

The ET tube cap embodiment 1100 further considering the ET tube cap 1100 being configured to receive the ET tube 1016 at the ET tube receiving aperture 1104.

The ET tube cap embodiment 1100 further imagining the ET tube cap 1100 being replaced by a ventilator cap that connects to the ventilator after the ET tube 1016 is fully deployed in a patient.

Yet another embodiment of the present invention contemplates a method comprising: providing an ET tube cap 1100 that comprises a tubular housing 1110 defined between an ET tube receiving aperture 1104 and a cap top 1130, an intake tube 1120 that extends from the tubular housing 1110, the intake tube 1120 defining a passageway between a proximal tube end 1125 and a distal tube end 1126, and a pressure relief valve 1115. Next, inserting an ET tube 1-16 into the ET tube receiving aperture 1104. This is followed by flowing oxygen through the ET tube 1016 from an oxygen source connected to the intake tube 1120. After this step, then intubating a patient while the oxygen is flowing through the ET tube 1016. Once the patient is intubated, replace the ET tube cap 1100 with a ventilator connector that connects the ET tube 1016 to a ventilator.

The method embodiment can be further envisioned to comprise a step for causing the pressure relief valve 1115 to open when pressure inside of the ET tube cap 1100 reaches a predetermine pressure limit. This can further comprise producing an audible alarm when the pressure relief valve 1115 opens. The audible alarm can be a whistle created by air flowing through the slits 1116 and the pressure relief valve 1115.

The method can further comprise inserting a stylet through the ET tube 1016 and into the patient via an instrument port 1101 in the cap top 1130. The ET tube cap 1100 can comprise an instrument port valve 1106 that blocks all airflow through the instrument port 1101 when the stylet is not inserted through the cap top 1130. The method embodiment can further be wherein the tubular housing 1110 consists of three apertures that are 1) an oxygen intake port

1122, 2) a pressure relief valve aperture 1114, and 3) the ET tube receiving aperture 1104. That is, no other apertures.

Still yet another embodiment of the present invention is envisioned to be a non-ventilator ET tube cap 1100 comprising: an oxygen source connector 1120 configured to connect to an oxygen source via an oxygen tube 1018; an ET tube receiving aperture 1104 that is specifically arranged to engage an ET tube 1016 in a removable relationship prior to the ET tube 1016 connected to a ventilator while the ET tube 1016 is deployed in a patient; and a pressure relief valve 1115 that opens when pressure inside of the ET tube cap 1100 exceeds a predetermined pressure threshold. A non-ventilator ET tube cap 1100 is defined herein as an ET tube cap 1100 that is a) not intended to be used with a ventilator, and b) is never used with a ventilator. Rather a ventilator connector is used to replace the non-ventilator ET tube cap 1100. Modification of the non-ventilator ET tube cap 1100 will necessarily change the principle of operation of the non-ventilator ET tube cap 1100.

The non-ventilator ET tube cap embodiment 1100 can be further envisioning the pressure relief valve 1115 comprising a whistle that produces sound when the pressure relief valve 1115 is opened.

The non-ventilator ET tube cap embodiment 1100 can be further envisioned to comprise an instrument port 1101 located at the cap top 1130.

The non-ventilator ET tube cap embodiment 1100 can optionally be further considered to be defined as consisting of three apertures that are 1) an oxygen intake port 1122, 2) a pressure relief valve aperture 1114, and 3) the ET tube receiving aperture 1104.

The above sample embodiments should not be considered limiting to the scope of the invention whatsoever because many more embodiments and variations of embodiments are easily conceived within the teachings, scope and spirit of the instant specification.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended embodiments are expressed. For example, though the embodiments teach a cap 300 possessing orifices extending from the side of being rotated about a cap body 302, other embodiments envisioned could equally be used while still maintaining substantially the same functionality without departing from the scope and spirit of the present invention. Though examples described herein are directed to the instrument port 1101 adapted to cooperate with a bronchial scope or stylet, a skilled artisan will appreciate that other instruments could be used with the instrument port 101 without departing from the scope and spirit of the present invention. Other embodiments envision a portion of the inventive concepts being used individually or in combination with other inventive concepts. Yet other embodiments envision different kinds of air feed systems for the cap or the novel ET tube 102 being electronically actuated or button actuated instead of by a rotating cap 300. Further, the terms "one" is synonymous with "a", which may be a first of a plurality.

It will be clear that the present invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the invention disclosed.

What is claimed is:

1. A method comprising:
   providing an endotracheal (ET) tube cap that comprises:
      a tubular housing defined by a cylindrical wall that extends between a first end and a second end, wherein a closed top surface covers the first end, an ET tube receiving aperture at the second end is configured to receive an ET tube,
      the cylindrical wall defining a cylinder interior surface and a cylinder exterior surface, the cylindrical wall further defining a cylinder interior volume bounded by the cylinder interior surface from the first end to the second end,
      the closed top surface permanently blocking all access to the interior volume from the first end,
      wherein access points to the interior volume through the cylindrical wall consist of a first element, a second element and a third element, all of which extend from the cylinder exterior surface,
      wherein the first element is an intake tube comprising an unobstructed passageway between a proximal tube end and a distal tube end; and
   the second element is a first pressure relief valve and the third element is a second pressure relief valve, the first and the second pressure relief valves are configured to open when pressure inside of the ET tube cap exceeds a predetermined pressure threshold;
   inserting the ET tube into the ET tube receiving aperture;
   flowing oxygen through the ET tube from an oxygen source connected to the intake tube;
   intubating a patient while the oxygen is flowing through the ET tube; and
   replacing the ET tube cap with a ventilator connector that connects the ET tube to a ventilator.

2. The method of claim 1, further comprising the first and the second pressure relief valves opening and producing an audible alarm.

3. The method of claim 2, wherein the audible alarm is a whistle created by air flowing through slits in the first and the second pressure relief valves.

4. A method comprising:
   providing an endotracheal (ET) tube cap that comprises:
      a housing extending from a top end to bottom end where an ET tube receiving aperture is located, the ET tube receiving aperture is configured to receive an ET tube,
      a closed surface covers the top end,
      the housing is tubular and defines an interior surface and an exterior surface, the housing further defining an interior volume bounded by the interior surface from the top end to the bottom end, wherein access points to the interior volume through the housing consist of a first pressure relief valve, a second pressure relief valve, the ET tube receiving aperture and an intake tube,
      the intake tube extends from the exterior surface and comprises an unobstructed passageway between a proximal tube end and a distal tube end; and
      wherein the first and the second pressure relief valves are configured to open when pressure inside of the ET tube cap exceeds a predetermined pressure threshold;
   inserting an ET tube into the ET tube receiving aperture;
   flowing oxygen through the ET tube from an oxygen source connected to the intake tube;
   intubating a patient while the oxygen is flowing through the ET tube; and
   replacing the ET tube cap with a ventilator cap that connects the ET tube to a ventilator.

5. The method of claim 4, wherein a laryngoscope blade is used during the intubating step.

6. An endotracheal (ET) tube arrangement comprising:
   an ET tube;
   an ET tube cap for connecting the ET tube to a pressurized oxygen source, wherein the pressurized oxygen source is configured to flow oxygen through the ET tube cap and out from a distal end of the ET tube;
   a ventilator cap for replacing the ET tube cap on the ET tube for alternatively connecting the ET tube to a ventilator;
   the ET tube cap comprising:
      a housing that extends from a first end to a second end comprising an ET tube receiving aperture that is configured to receive the ET tube,
      the housing defining an interior surface and an exterior surface, the housing further defining an interior volume bounded by the cylinder interior surface from the first end to the second end,
      wherein access points of the housing consists of four access points to the interior volume through the housing, the four access points consist of a first pressure relief valve, a second pressure relief valve, the ET tube receiving aperture and an intake tube that extends from the exterior surface, and
      wherein the intake tube comprises an unobstructed passageway between a proximal tube end and a distal tube end.

7. The ET tube arrangement of claim 6, wherein the housing is tubular.

8. The ET tube arrangement of claim 6, wherein the first end is a closed surface.

9. The ET tube arrangement of claim 6, wherein the first and the second pressure relief valves are configured to produce an audible alarm when the first and the second pressure relief valves open.

* * * * *